US012728423B2

(12) United States Patent
Schmidt

(10) Patent No.: US 12,728,423 B2
(45) Date of Patent: Sep. 8, 2026

(54) THAWING DEVICE FOR THAWING A MEDIUM, AND A METHOD FOR THAWING A MEDIUM

(71) Applicant: AGENTUR LEVEN GMBH, Cologne (DE)

(72) Inventor: Günther Schmidt, Bonn (DE)

(73) Assignee: AGENTUR LEVEN GMBH (DE)

( * ) Notice: Subject to any disclaimer, the term of this patent is extended or adjusted under 35 U.S.C. 154(b) by 570 days.

(21) Appl. No.: 18/035,275

(22) PCT Filed: Nov. 5, 2021

(86) PCT No.: PCT/EP2021/080823
§ 371 (c)(1),
(2) Date: May 3, 2023

(87) PCT Pub. No.: WO2022/096674
PCT Pub. Date: May 12, 2022

(65) Prior Publication Data
US 2024/0351043 A1 Oct. 24, 2024

(30) Foreign Application Priority Data
Nov. 6, 2020 (DE) ..................... 10 2020 129 292.9
Feb. 15, 2021 (EP) .................................... 21157125

(51) Int. Cl.
*B01L 7/00* (2006.01)
*A61M 1/02* (2006.01)
*A61M 5/44* (2006.01)

(52) U.S. Cl.
CPC ............ *B01L 7/00* (2013.01); *A61M 1/0281* (2013.01); *A61M 5/445* (2013.01);
(Continued)

(58) Field of Classification Search
CPC .......... B01L 7/00; B01F 35/513; B01F 35/92; B01F 31/24; B01F 31/25; A61M 5/445; A61M 1/0281
(Continued)

(56) References Cited

U.S. PATENT DOCUMENTS 117,733 A * 8/1871 Black ........................ F16D 3/72 126/41 R
1,498,072 A * 6/1924 Breeze ...................... F16D 3/66 464/81

(Continued)

FOREIGN PATENT DOCUMENTS

CN 107397984 A 11/2017
DE 2418155 A1 12/1975

OTHER PUBLICATIONS

English Translation of CN 107397984 A (Year: 2025).*

*Primary Examiner* — David L Sorkin
(74) *Attorney, Agent, or Firm* — Lisa E. Geary; Eckert Seamans Cherin & Mellott LLC

(57) ABSTRACT

The present invention relates to thawing devices for thawing a substrate (1), in particular blood plasma, which is in a frozen aggregate state, wherein the substrate (1) is contained in a container (2), in particular a bag.
Compared to the prior art, the thawing devices proposed by the invention enable a shorter thawing time as well as a gentle thawing process at the same time.
Also, the present invention proposes methods for thawing a substrate (1) in a frozen aggregate state.

18 Claims, 12 Drawing Sheets

Figure 1:
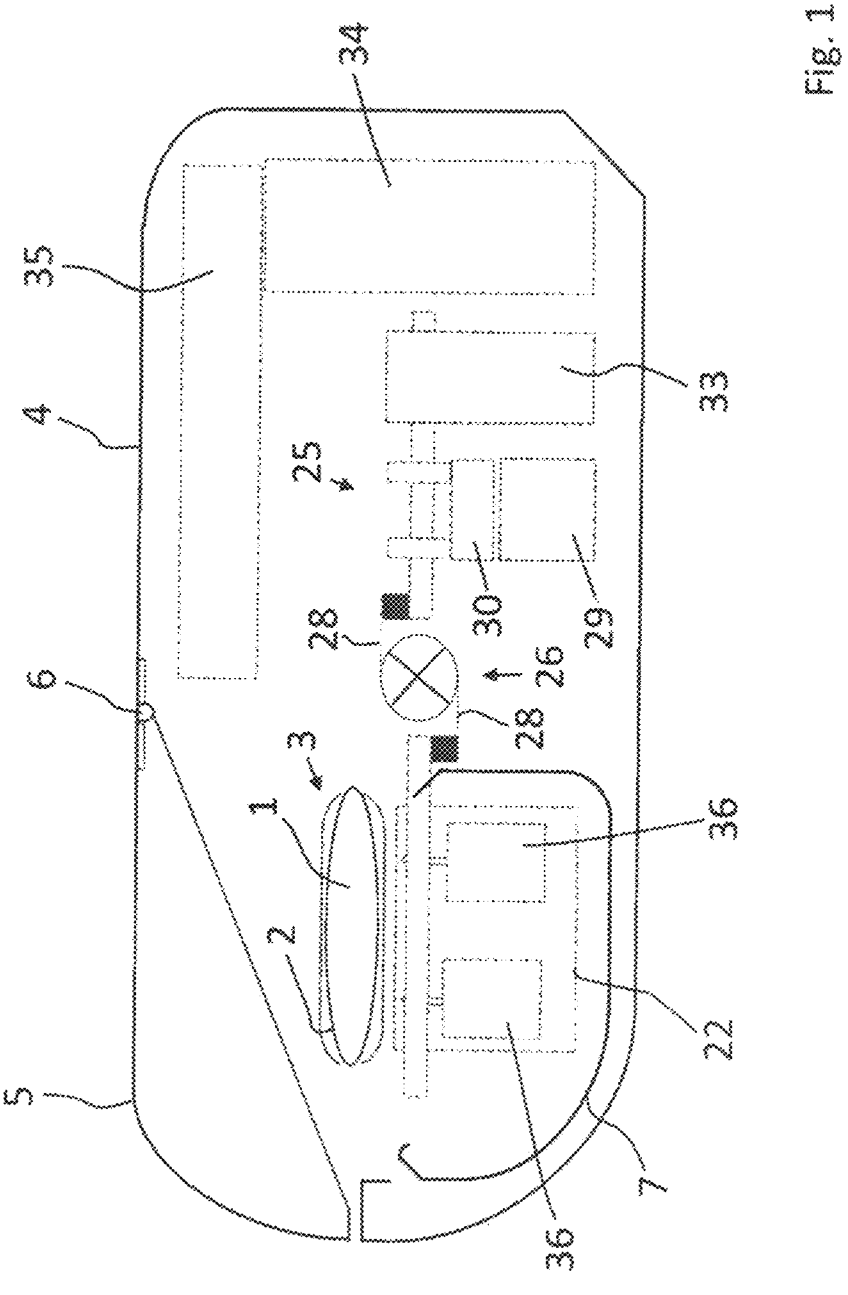

(52) U.S. Cl.
CPC ... *B01L 2200/141* (2013.01); *B01L 2200/147* (2013.01); *B01L 2200/18* (2013.01); *B01L 2300/123* (2013.01)

(58) Field of Classification Search
USPC ......................... 366/145, 146, 209, 212, 216
See application file for complete search history.

(56) References Cited

U.S. PATENT DOCUMENTS

| | | | | | |
|---|---|---|---|---|---|
| 2,426,976 | A * | 9/1947 | Taulman | F16L 53/35 | 219/535 |
| 2,700,097 | A * | 1/1955 | Morey | A47J 36/2433 | 219/441 |
| 2,914,445 | A * | 11/1959 | Clarke | A61K 35/50 | 424/583 |
| 4,034,602 | A | 7/1977 | Woo et al. | | |
| 4,473,739 | A | 9/1984 | Scheiwe et al. | | |
| 4,742,202 | A | 5/1988 | Campbell et al. | | |
| 5,261,255 | A | 11/1993 | Coelho et al. | | |
| 5,427,451 | A * | 6/1995 | Schmidt | B01F 31/22 | 366/208 |
| 5,611,921 | A * | 3/1997 | Deskins | B01D 24/22 | 210/219 |
| 7,210,843 | B2 * | 5/2007 | Friedman | B01F 31/27 | 366/110 |
| 2004/0109385 | A1 * | 6/2004 | Wisniewski | A61M 1/025 | 366/208 |
| 2004/0265168 | A1 | 12/2004 | Bakke | | |
| 2006/0032607 | A1 | 2/2006 | Wisniewski | | |
| 2013/0039145 | A1 * | 2/2013 | Pollaro | B01F 31/201 | 366/237 |
| 2015/0122793 | A1 | 5/2015 | Takizawa | | |
| 2017/0036181 | A1 | 2/2017 | Boettcher et al. | | |
| 2019/0336660 | A1 | 11/2019 | Shavit et al. | | |
| 2021/0145695 | A1 * | 5/2021 | Sanchez | A61J 1/16 | |
| 2022/0170694 | A1 * | 6/2022 | Cutting | F25D 25/00 | |
| 2024/0228933 | A1 * | 7/2024 | Veraitch | C12M 27/16 | |

* cited by examiner

E
33
25
23
30
29
32
21
28
31 26
28
24
2
3
1
27

18
16
19

17
15
20

H
2
22
51
57
56
47
39
49
38
48
102
38
40
41
50
48
101
38
53
52
58
55
54
9
8

33
32
30
59
60
61
28
63
62
29

3
2
4
8
9
10
13
80
82
84
86
88
90
92
94
96
98
100
102
104
106
108
110
112
114
116
118

THAWING DEVICE FOR THAWING A MEDIUM, AND A METHOD FOR THAWING A MEDIUM

The present invention relates to a thawing device for thawing a substrate, which is in a frozen aggregate state, in particular blood plasma, wherein the substrate is contained in a container, in particular a bag. The thawing device comprises a receiving unit for arranging the container containing the substrate, the receiving unit having a heating device for providing thermal energy required for thawing the substrate. Furthermore, the thawing device comprises a first movement device, which is arranged to transmit a first movement to the receiving unit as well as the container received therein together with the substrate, wherein the first movement is a movement executed substantially in a plane, in particular a linear movement.

Furthermore, the invention relates to a method for thawing a substrate in a frozen aggregate state, in particular blood plasma, wherein the substrate is contained in a container, in particular a bag.

Thawing devices for thawing medical substrates are well known from the prior art. By way of example, reference should first be made to the publication DE 195 48 826 A1, which discloses a generic thawing device. The problem described there can be transferred—at least in parts—to the present invention, which is why the problem already described in DE 195 48 826 A1 will be mentioned below.

As described there, it is common in clinical practice to dilute active pharmaceutical ingredients supplied by industry in standard concentrations and standard volumes with carrier solutions to patient-specific concentrations and to administer them. Since these individually prepared preparations are often used in long-term therapies, a correspondingly large total volume is used in the preparation of the patient-specific active ingredient mixture. The partial volumes of the total volume intended for individual administration must therefore be filled into syringes or other containers and then stored frozen. Only in this way can the active ingredients, which are generally thermally labile, be preserved over the required long periods.

One problem with this established and widely used conventional preservation method is that a relatively long thawing time must be provided for each individual sample. This is also particularly inconvenient in that the time of administration of the next volume of active ingredient cannot be precisely predicted. Although a schedule for the administration of the active ingredient volumes is drawn up for the individual patient, as a rule a blood sample is first taken from the patient in order to decide only after its analysis whether and—if so—at what precise time the next partial volume of active ingredient can be applied. This procedure therefore often leads to schedule shifts and consequently to the loss of the previously thawed active ingredients.

This problem was countered with the rapid thawing device described there.

Likewise, it was already problematized in DE 195 48 826 A1 that frozen liquids can be thawed on the basis of microwave thawing devices, which are thereby heated by microwave radiation at frequencies between 2.425 and 2.475 GHz. However, these have the disadvantage that predominantly the frozen liquid is heated strongly due to the focusing of the radiation in a certain area of the frozen liquid, so that a uniform heating of the frozen liquid is prevented. Heating the frozen liquid only in a certain area may cause damage to ingredients or active ingredients of the liquid, so that chemical modification of the ingredients or active ingredients is to be expected. In addition to chemical modification of the (thawed) drugs, denaturation of vaccines, proteins or sera in the infusion and injection solutions can also occur through the application of microwave radiation, depending on the type of substrate.

Manual thawing of substrates contained in containers under warm, running water can lead to contamination of the substrate by microorganisms, which can enter the container from outside through opening gaps, leaks or the like. Even heating by means of the user's palm does not exclude such contamination by microorganisms. In addition, thawing in the hands of a user requires a relatively large amount of time. However, it is urgently necessary and vital, especially in hospitals during daily routine work, emergency wards or in the event of accidents on site, to be able to thaw and apply medical substrates quickly.

To circumvent these problems, DE 195 48 826 A1 proposes to additionally set the substrate to be thawed in motion during heating (via heating elements, not a microwave device) by means of a shaking mechanism. Although this technique allows a thawing process that is gentler on the substrate than a microwave-based thawing process and a faster thawing process than the manual methods described, the thawing times are not sufficient for certain medical substrates or applications. One such example of a medical substrate for which storage in a frozen aggregate state is common and rapid thawing is essential is blood plasma. Blood plasma is usually stored (preserved) at −30 to −40° C., but can only be administered in a liquid aggregate state (i.e. thawed).

Blood plasma must be quickly available and applicable during large, complicated operations and especially in emergencies in order to counteract massive blood losses of patients (e.g. casualties of an accident). Such high blood losses can also occur during transplantations, necessitating the rapid availability of blood plasma.

Since thawing times of approx. 30 minutes can be realized with conventional devices and methods (e.g. known from DE 195 48 826 A1), blood plasma is often thawed to "stock" for upcoming operations so that it is immediately available when needed. Plasma that is not needed is disposed of after the operation, which has a negative effect on the already scarce stocks of blood plasma.

Providing shorter thawing times for frozen blood plasma is thus of significant interest in ensuring efficient and life-saving patient care. At the same time, it is important to ensure that the blood plasma is thawed gently.

Accordingly, the present invention is based on the task of proposing a thawing device and a method for thawing a substrate, in particular blood plasma, which is in a frozen aggregate state, whereby a shorter thawing time is made possible in comparison with the prior art and, at the same time, a gentle thawing process is made possible.

The aforementioned problem is solved with a thawing device for thawing a substrate in a frozen aggregate state, the substrate being contained in a container, the thawing device comprising: a receiving unit for arranging the container containing the substrate, the receiving unit having a heating device for providing thermal energy required for thawing the substrate; a first movement device configured to transmit a first movement to the receiving unit and the container received therein together with the substrate, wherein the first movement is a movement executed essentially in a horizontal plane; and a second movement device configured to transmit a second movement to the receiving unit and the container received therein together with the substrate, wherein the second movement is a fulling movement, wherein the second movement device comprises at least one second movement unit configured to exert a vertical lifting movement on the receiving unit, wherein, when the vertical lifting movement is exerted, a partial deformation of the receiving unit is produced, the partial deformation having an extent corresponding to a thawed portion of the substrate, as well as with a method for thawing a substrate with the thawing device, wherein the substrate is in a frozen aggregate state, and wherein the substrate is contained in a container, the method comprising: arranging the container containing the substrate in the receiving unit, heating the substrate contained in the container with the heating device, wherein during the heating process: a first movement is transmitted by the first movement device to the receiving unit and the container received therein together with the substrate, the first movement being a movement executed substantially in a horizontal plane, and a second movement is transmitted by the second movement device to the receiving unit and the container received therein together with the substrate, the second movement being a fulling movement.

It should be noted that the features listed individually in the claims can be combined with each other in any technically useful manner and show further embodiments of the invention. The description additionally characterizes and specifies the invention, particularly in connection with the figures. Also, the features described in connection with the thawing devices according to the invention may be advantageous embodiments of the methods according to the invention and vice versa. It should also be noted that those features described in relation to the thawing device according to claim 1 can be, as it were, advantageous design features of that claim 18 also relating to a thawing device, and vice versa.

It should also be noted that a conjunction "and/or" used herein that stands between and links two features should always be interpreted to mean that in a first embodiment of the subject matter of the invention, only the first feature may be present, in a second embodiment, only the second feature may be present, and in a third embodiment, both the first and second features may be present.

As mentioned, the present invention relates firstly to a thawing device for thawing a substrate, in particular blood plasma, which is in a frozen aggregate state, the substrate being contained in a container, in particular a bag, the thawing device comprising a. a receiving unit for arranging the container containing the substrate, the receiving unit comprising heating means for providing thermal energy required for thawing the substrate;

b. a first movement device, which is set up to transmit a first movement to the receiving unit as well as the container received therein together with the substrate, wherein the first movement is a movement executed essentially in a plane, in particular a linear movement.

According to the invention, the thawing device is characterized by c. a second movement device, which is set up to transmit a second movement to the receiving unit as well as the container received therein together with the substrate, wherein the second movement is a fulling movement. The first and second movement devices are assembled on one or more stable (positionally fixed) base plates.

The thawing device can be set up for parallel thawing of a plurality of substrates contained in individual containers, in particular blood plasma. For simplicity, the following comments refer to the description of those design features that are required for thawing substrate contained in a single bag. In the thawing device, the described features can thus readily be present in a plurality, i.e., the thawing device can comprise a plurality of thawing units, in each of which a substrate contained in a single container can be thawed. The following explanations therefore refer to a single thawing unit.

For the purposes of the invention, a "substrate" may in particular be understood to mean a medical substrate. A "medical" substrate is primarily used in the field of medicine, e.g. for intravenous or injection treatment of patients. In order to use the medical substrate (e.g., for administration to a patient), it must be in a liquid form. It does not have to be a (pure) liquid composed of a single chemical compound in the proper (chemical) sense. For example, the substrate can be a homogeneous or heterogeneous mixture of substances. An example of a homogeneous mixture of substances is a solution. Heterogeneous substance mixtures can be emulsions, suspensions or foams. Also, fine particles (e.g. nanoparticles, proteins, etc.) can be distributed as solids in a liquid or a mixture of several liquids. In this context, a "liquid" can also be understood to be a pasty or viscous mass which, for example, has a significantly reduced flowability compared to water. As mentioned, the substrate is in a frozen aggregate state before the thawing process. To undergo a thawing process in thawing device according to the invention, the substrate may be completely or partially frozen. For example, it is conceivable that the substrate is subjected to a pre-thawing process before thawing in the thawing device, for example by thawing at room temperature, so that the substrate is already thawed to a certain extent before the actual thawing in the thawing device. In particular, a "substrate" may be understood to mean a blood preparation such as blood plasma.

Nonetheless, a "substrate" may also be a substrate of some other kind, such as a food, feed, chemical, medical analyte, or the like.

The substrate is contained or stored in a container. The container can be hermetically sealed or even kept under vacuum seal. Furthermore, in addition to the substrate, an inert gas (e.g. $N_2$) may be present in the container. The container can have an opening device, which can be opened once or several times and closed again. The container may in particular be a bag, preferably a medical bag. These are frequently disposable medical bags made of plastic.

The particular advantages of a thawing device according to the invention are explained below using the example of the thawing process of blood plasma as the substrate to be thawed. In thawing devices known from the prior art (without microwave heating), i.e. e.g. in the device according to DE 195 48 826 A1, the uppermost layer of the frozen blood plasma is initially heated relatively quickly during thawing. This causes a thin liquid film to form on the surface of the blood plasma, which remains in this liquefied state. As a result, the original temperature difference between the liquid film and the heating element is drastically reduced. Accordingly, starting from the heating element, the heat can only be inadequately tracked in the direction of the inner (still frozen) blood plasma in order to also supply the inner layers of the blood plasma sufficiently with heat and to bring them to thaw quickly. This results from the fact that, by means of temperature sensors present in the thawing device and associated with a heating control system, essentially only the temperature of the outer (already melted) liquid film is detected. However, since the heat supply is controlled based on the measured temperature difference between molten blood plasma (measured by the temperature sensors) and the heating element, the temperature difference between the interior of the blood plasma and the heating element is not taken into account. Consequently, too little heat is supplied to the system to allow sufficiently rapid thawing of the blood plasma.

) When thawing blood plasma (or other substrates) with a thawing device according to the invention, on the other hand, the movements exerted on the blood plasma (the first movement and second or further movement exerted via the first and second or further movement devices, respectively) ensure that already liquefied (thawed) blood plasma cools continuously and settles to temperatures of 0° C. to 5° C. The movements are performed until all the blood plasma has liquefied (thawed). The particular advantage of this procedure is the resulting (largely greater) temperature difference between the blood plasma and the heating element(s) of the thawing device. Thus, the heat transfer to the interior of the substrate (e.g., the blood plasma) can be more efficiently replenished and more evenly distributed relative to the total volume of the substrate contained in the container. This further reduces the thawing time compared to thawing devices known in the prior art. Relative to a volume of 300 mL of blood plasma as substrate, contained in a plasma bag as container, thawing times of 5-8 minutes can be achieved with a thawing device according to the invention, but in particular thawing times of 6-8 minutes.

The aforementioned receiving unit is designed for temporary arrangement and/or fastening of the container (together with the substrate contained therein). The receiving unit can partially or completely enclose the container in a state according to the application. The receiving unit may be formed in one or more parts. As mentioned, the receiving unit comprises a heating device for providing thermal energy required for thawing the substrate. In particular, the heating device is a device for emitting thermal radiation, but preferably not microwave radiation. Advantageously, the heating device may be designed or arranged such that it uniformly surrounds a container placed in the receiving unit. Uniform heat transfer is advantageous for ensuring a gentle and rapid thawing process. The heating device is connected to a control and regulation device. Furthermore, at least one temperature sensor, preferably several temperature sensors, is associated with the control and regulation device, by means of which the temperature of the substrate to be thawed (at least in the surface region) can be detected. Depending on the measured temperature, the heat supply can be adjusted. The control and regulation can be automated.

A collecting tray can be provided below the receiving unit, in which moisture, overflowing substrate or the like can be collected. This prevents impurities or moisture from accumulating in the thawing unit. The collecting tray can be removed from the thawing unit for emptying.

The first movement transmitted by the first movement device to the receiving unit and the container and substrate received therein is preferably a shaking movement in the sense of a back and forth movement executed in one plane. The shaking movement is executed with a frequency of about 20 Hz and preferably comprises a movement of about 10 mm. The shaking motion can be a linear motion, but also a motion guided in a circle. More complex motion sequences (motion patterns) executed in a plane are also conceivable. The plane can be a horizontal plane, but also a plane arranged elsewhere in space (e.g. inclined). As mentioned, the movement is "essentially" in a plane. This means that the main direction of movement is within a plane, but nevertheless minor deviations are opened. Such deviations can result, for example, from imbalances, weight distributions or the like.

The second movement exerted by the second movement device on the receiving unit and the container and substrate received therein is—as mentioned—a fulling movement. When a "fulling movement" (also referred to as "fulling") is performed, the container together with the substrate contained therein is at least partially deformed. The process of "fulling" can also be understood as kneading or pressing. According to the invention, both the first movement and the second movement (fulling movement) are exerted in parallel and transferred to the receiving unit and the container and substrate received therein. This enables a better mixing of the substrate during thawing together with an associated more uniform heat transfer to the substrate, a decisive factor for reducing the thawing time.

Further advantageous embodiments of a thawing device according to the invention result from the features indicated in the subclaims, as well as those described below. The features indicated in the subclaims are also described below. It should be emphasized at this point that the features described below can without further ado also be advantageous design features of the method according to the invention. In order to avoid repetition, the features in question are described below only in relation to the thawing device according to the invention.

According to a first advantageous embodiment of the invention, in a thawing device according to the invention, it may be provided that the receiving unit is formed in the shape of a shell, wherein the shell comprises a first half shell and a second half shell, wherein the first half shell is a lower half shell and the second half shell is an upper half shell, and wherein the first and second half shells are detachably connectable to each other. A shell shape is advantageous with respect to securely locating the receptacle in the receiving unit without the risk of the receptacle being moved out of the receiving unit during the transfer of motion. The shape of the receiving unit is not limited to a shell shape. The half-shells may have, at least in part, a different pliability and/or deformability. By a "deformability" is meant in particular a reversible (elastic) deformability. Thus, it is advantageous if the lower half-shell has at least partially a higher pliability and/or deformability than the upper half-shell. This is because the fulling movement exerted on the receiving unit, i.e. the shell, is primarily exerted on the lower half-shell. This deformability (material flexibility) is necessary to allow a flexible change in the shape of the container during fulling. This is because the shape of the container changes permanently during the thawing process.

According to a further advantageous embodiment of the invention, a thawing device according to the invention may provide that the first and second half-shells are adapted to the shape of the container, the first and second half-shells at least partially surrounding the container when it is arranged in the shell. The shape matching of the first and second half-shells to the shape of the container ensures a secure fit of the container in the receiving unit. The shape, size, and material construction of the first and second half-shells may be configured to compensate for expansion of the container during thawing of the substrate. Preferably, the first and second half-shells expand by an amount corresponding to the volume expansion of the substrate, if any. Alternatively, it may be provided that the receiving volume of the receiving unit is slightly larger than the volume of the container so that the container can be placed in the receiving unit with some clearance. For example, the half-shells may have a rectangular half-shell base, wherein the shell shape is provided by sidewall portions adjacent to side portions of the half-shell base and extending along a longitudinal half-shell axis. Preferably, those sidewall portions of the lower half-shell are formed to be flexible, while the sidewall portions of the upper half-shell are formed to be dimensionally stable, i.e. rigid.

According to a further advantageous embodiment of the invention, it can be provided in a thawing device according to the invention that fixing means are provided on the first and second half-shells, with which the container can be fixed. The fixing means may be realized, for example, in the form of tabs or retaining clips formed or arranged on the respective half-shells, which cooperate with fixing means corresponding thereto and arranged or formed on the respective opposite half-shell. The fixing means cooperating with the tabs or retaining clasps can be fastening openings, Velcro elements, clamping elements or the like. Also, the fixation can be realized by snap fasteners.

According to a further advantageous embodiment of the invention, it can be provided in a thawing device according to the invention that the first and second half-shells each have a multilayer layer structure, a heating element being provided in each case in one layer of the layer structure of a respective half-shell. The heating elements of the respective half shells provide the heating device. The heating elements may be signal-connected to the aforementioned control and regulation device. Also, the heating elements have an electrical supply line. The heating elements can extend along the half-shell (in particular over the surface of the half-shell base) in a meandering or spiral manner, and the heating elements can be formed of stainless steel, for example. Preferably, the heating elements have a thickness of 50 μm. With heating elements made of stainless steel, the width of the heating elements as well as the maximum heating can be increased compared to conventional copper elements. The respective heating element can also be in the form of a heating foil.

The multilayer structure of the half-shells can preferably be composed as follows. Facing the container arranged in the receiving unit, the half-shells have an outer skin or a support layer for supporting the container. This can preferably be made of stainless steel and preferably have a thickness of 100 μm to 150 μm. This can be followed by an electrical insulation layer, preferably 50 μm thick, which can be made of a polyimide film, for example. The layer comprising the heating element can follow the insulation layer, whereby this layer can have a thickness of 50 μm. The layer comprising the heating element can be in the form of a stainless steel foil, but can also be made of an electrically insulating material in which one or more stainless steel heating elements are integrated. This can be followed by a support or insulation layer, which can preferably be formed from a glass-fiber-reinforced plastic and can have a thickness of 0.3 mm. This can be followed by a mounting support for the heating shell, which can be made of aluminum and have a thickness of 0.5 to 1.0 mm.

According to a further advantageous embodiment of the invention, it can be provided in a thawing device according to the invention that the first movement device comprises a linear drive which is in mechanical operative connection with at least one movably mounted guide unit via a mechanical coupling device, the at least one guide unit being mechanically operatively connected to the receiving unit for transmitting the first movement. The mechanical coupling device can be of any type as long as it is suitable for transmitting the first movement generated by the linear drive to the receiving unit. It is also conceivable that it is an electrical coupling device. A "mechanical active connection" can be understood as any connection by means of which motion transmissions between two components can be enabled or mediated. A mechanical active connection can be provided by a direct mechanical connection of two components, but also by one or more intermediate components arranged between two components to be connected in a motion-transmitting manner. The linear drive generates a translatory motion which is transmitted to the pick-up unit. In this case, the movement can be a linear movement or another movement with a predetermined course. The linear drive can be a threaded rod drive (ball screw drive), a roller screw drive, a hydraulic drive, a pneumatic drive or an electromechanical linear drive (e.g. a linear motor).

According to a further advantageous embodiment of the invention, it can be provided in a thawing device according to the invention that the mechanical coupling device is a cross-spring joint which is arranged between the linear drive and the at least one guide unit and is connected both to the linear drive and to the at least one guide unit or to a component operatively connected thereto via a connecting means, for example a stainless steel strip. Instead of a stainless steel strip, the connecting means can also be another force transmission means, for example a tension band, a chain, a spring or the like. Cross-spring joints are characterized by their freedom from friction, lubrication and maintenance.

According to a further advantageous embodiment of the invention, in a thawing device according to the invention it may be provided that the linear drive is connected to a mechanical or electrical spring system, which is arranged to adjust running characteristics and efficiency of the linear drive. The aforementioned mechanical coupling between the linear drive and the at least one guide unit (using the mechanical coupling device) provides a mechanical oscillating circuit. This is supported by the aforementioned mechanical or electrical spring system, whereby in particular the efficiency and smooth running of the oscillating circuit can be improved. A mechanical spring system can comprise an adjustable band spring. An electric spring system can comprise a transformer with a movable yoke, which is preferably coupled in combination with a linear drive designed as a reluctance motor.

According to a further advantageous embodiment of the invention, it can be provided in a thawing device according to the invention that the linear drive is an electromechanical linear drive which has at least one stator arrangement and one rotor arrangement, the rotor arrangement being connected to the mechanical coupling device via the connecting means, in particular the stainless steel strip. The electromechanical linear drive is preferably a linear motor, with which translatory feed movements can be generated. A linear motor is the linear design of a rotating machine, which can be imagined as the unwinding of a rotary motor cut open to the center. It consists of a current-carrying primary part (comparable to the stator of a rotary motor, referred to here as the stator arrangement) and a reaction or secondary part (comparable to the rotor of a rotary motor, referred to here as the rotor arrangement). Linear motors can be synchronous linear motors, asynchronous linear motors, stepper linear motors or DC linear motors. While the stator arrangement in the asynchronous design is equipped with short-circuit bars, this consists of permanent magnets in the synchronous motor. The linear drive can also be a reluctance motor, which comprises a stator arrangement and a rotor arrangement.

According to a further advantageous embodiment of the invention, it can be provided in a thawing device according to the invention that the at least one guide unit and the rotor arrangement are each movably mounted on guide rods, the guide rods preferably being arranged in a common plane. Preferably, the bearings of the at least one guide unit and the rotor arrangement on the respective guide rods are plain bearings. The movement of the rotor arrangement and the at least one guide unit are preferably counter-rotating. Furthermore, it must be ensured that the rotor arrangement and the guide unit (together with the components connected thereto) have approximately the same weight mass, since otherwise undesirable imbalances can arise in the movement sequence. A pivot point is required for the above-mentioned counter-rotating movements, provided here by the coupling device, in particular the universal joint. The cross-spring joint is frictionally connected to the rotor arrangement and to the at least one guide unit or a component operatively connected thereto via a connecting means, for example a stainless steel strip. In a preferred embodiment, the guide rods can run horizontally and be arranged in alignment with one another. Instead of separate guide rods guiding the rotor arrangement and the at least one guide unit, a common guide rod can also be provided to guide the rotor arrangement and the at least one guide unit.

According to a further advantageous embodiment of the invention, it can be provided in a thawing device according to the invention that the second movement device comprises at least one second movement unit which is set up to exert a lifting movement on the receiving unit, in particular the lower half-shell, wherein, when the lifting movement is exerted, a partial deformation of the receiving unit, in particular of the lower half-shell, is effected to an extent corresponding to a thawed portion of the substrate. This is because the substrate can only be deformed in an at least partially thawed state. The greater the proportion of thawed substrate, the greater the lifting motion that can be transmitted to the substrate. When the lifting motion is exerted on the lower half shell, it is lifted to the extent that substrate has already liquefied during the thawing process. Physically, frozen blood plasma (as an example of a substrate thawable by the thawing device of the invention) is in a crystalline state. As the blood plasma increasingly heats up during the thawing process, initially at the surface, the blood plasma increasingly changes to an amorphous state near the surface. As a result, the deformability of the blood plasma increases. The second movement device can comprise a plurality of second movement units which exert a lifting movement on the receiving unit, in particular the lower half-shell, at different spatial positions, so that a fulling movement is generated by the plurality of lifting movements. The lifting movements exerted with the second movement units at the respective different positions on the lower half-shell can be executed simultaneously or successively at all positions. It may also be provided for a lifting movement to be performed simultaneously at a predetermined number of positions. Preferably, the lifting movements are executed in such a way that continuously changing positions of the lower half shell (and thus of the container) are subjected to pressure. The second movement units can be controlled by control electronics (for example, a microcontroller) in a predetermined scheme, so that the second movement units can perform lifting movements in a desired sequence in the direction of the receiving unit and the container and substrate arranged therein. The stroke movements exert pressure on the blood plasma at continuously changing positions, causing the amorphous portion of the blood plasma to liquefy more quickly or thaw further than without the exerted fulling movement.

According to a further advantageous embodiment of the invention, it can be provided in a thawing device according to the invention that a force transmission element is arranged between the receiving unit, in particular the lower half shell, and the at least one second movement unit, which force transmission element is connected both to the receiving unit, in particular the lower half shell, and to the at least one second movement unit in order to transmit the lifting movement to the receiving unit, in particular the lower half shell. If several of the second movement units are provided, it is advantageous to provide a number of force transmission elements corresponding to the number of second movement units, and to arrange these in each case between the receiving unit and the respective second movement units and to connect them to both components. The force transmission element can be connected to a component belonging to the respective second movement unit, for example a housing.

In an alternative embodiment, the force transmission element can also be provided for transmitting the first movement in addition to the lifting movement. This is because the first movement (shaking movement) is transmitted to the container (including substrate) arranged in the receiving unit via the mechanical coupling/connection between the guide unit and receiving unit. If the guide unit is connected to the force transmission element, the first movement (shaking movement) can also be transmitted to the receptacle unit via the force transmission element. In this case, the force transmission element can thus be provided for transmitting the first and second movements. Also, in a further alternative embodiment, several guide units can be provided which are movably mounted either on a common guide rod or separate (in particular parallel arranged) guide rods. For synchronous motion transmission starting from the linear drive, the guide units can be mechanically connected to each other. It is also possible for the linear drive to be mechanically connected to the respective movably mounted guide units via a plurality of mechanical coupling devices. The mechanical coupling devices may each be universal joints, which may be arranged between the linear drive and the guide units, and may each be connected both to the linear drive and to a respective guide unit or a component operatively connected thereto via a connecting means, e.g. a stainless steel strip. If a plurality of guide units is provided, each guide unit may be connected to a force transmission element.

According to a further advantageous embodiment of the invention, it can be provided in a thawing device according to the invention that the force transmission element comprises a ball bearing, and that the force transmission element is attached to the receiving unit, in particular the lower half shell, via a welded joint. A ball bearing, in particular via a ball joint, is advantageous because the trigonometric conditions (due to the substrate always changing shape during thawing) always change with the force transmission. By means of a ball bearing, the force transmission paths can be adapted to the changed shape of the substrate contained in the container. Instead of a welded connection, another type of fastening can also be considered, for example a temperature-stable adhesive connection, or a mechanical connection (e.g. a riveted connection).

According to a further advantageous embodiment of the invention, it can be provided in a thawing device according to the invention that the at least one second movement unit comprises at least one lifting magnet, which is set up to transmit a stroke, in particular a lifting and lowering stroke, to the force transmission element, the receiving unit connected to the force transmission element and the container arranged in the receiving unit together with the substrate contained therein by carrying out lifting movements. If the second movement device comprises a plurality of second movement units, each of the second movement units may comprise a lifting magnet. When the lifting motion is performed, the stroke may first be transmitted from the lifting magnet to a linkage associated with the respective one of the second motion units. The linkage may be connected to a movably mounted carriage, the carriage being connected to the force transmission element. The carriage is movably mounted in such a way that it also tracks the first movement (shaking movement) triggered by the linear drive. The movable mounting of the carriage has the effect that the second movement units (for generating the fulling movement) are decoupled from the first movement or the associated oscillations. The second motion units thus preferably do not track the first motion. The carriage can be movably mounted on a guide rod mounted in a housing associated with a respective second motion unit.

According to a further advantageous embodiment of the invention, it can be provided in a thawing device according to the invention that the at least one second movement unit comprises at least one mechanical lifting device, which is set up to transmit a stroke, in particular a lifting and lowering stroke, to a force transmission pin arranged movably transversely, in particular perpendicularly, to the stroke axis by carrying out lifting movements.

The force transmission pin can be moved transversely, in particular perpendicularly, to the stroke axis between a first and a second position. In its second position, to transmit a lifting movement executed by the at least one mechanical lifting device to the force transmission element, the receiving unit connected to the force transmission element and the container arranged in the receiving unit together with the substrate contained therein. In particular, the force transmission pin may be arranged to transmit, in its second position, a lifting movement performed by the at least one mechanical lifting device to a component directly or indirectly connected to the force transmission element. In particular, it can be provided that the force transmission pin in its second position transmits the lifting movement to a housing part in which a carriage connected to the force transmission element is movably mounted. The carriage can be movably mounted on a guide rod arranged in the housing part. The movable mounting of the carriage has the effect that in this embodiment the second movement units (for generating the fulling movement) are decoupled from the first movement.

In the first position of the force transmission pin, no transmission of the stroke movement takes place in the direction of the force transmission element. The force transmission pin can be controlled by a control unit and moved back and forth via a movement mechanism transversely, in particular perpendicularly, to the stroke axis. The force transmission pin can be movably guided in a guide device, e.g. a guide groove. Such a variant requires less power than an embodiment based on lifting magnets. In this embodiment, the stroke movement can be generated by a geared motor driving a camshaft at about 60 rpm. The motion is first transmitted to a plunger connected to the camshaft and arranged for linear movement along the stroke axis, whereby the plunger can engage a (lower) end of the power transmission pin in the second position of the power transmission pin and transmit the stroke motion to it.

A further movement device can be provided. The further movement device can be set up to transmit a further movement to the receiving unit and the container and substrate received therein. The further movement preferably runs in a different direction than the first movement. Preferably, the further movement runs perpendicular to the plane in which the first movement of the first movement device is executed.

If the first movement is a linear movement, then the further movement is preferably perpendicular to this linear movement. The further movement can be vertical.

The further movement may be a fulling movement. The further movement device can be included in or form the second movement device.

In another advantageous embodiment of the invention, the further movement is not a fulling movement.

The receptacle unit, in particular the lower half-shell, can be flexible or deformable. Alternatively, the holder unit or one or both of the half-shells, in particular the lower half-shell, can be dimensionally stable, i.e. rigid.

For example, in the embodiment in which the receiving unit or one or both of the half-shell forms is dimensionally stable and/or in which the force transmission element has a planar force transmission area, the further movement is preferably not a fulling movement.

The further movement device can be provided in addition to the second movement device.

The further movement device can be set up to transmit the further movement directly to the pick-up unit. The further movement device can be set up to transmit the further movement indirectly to the pick-up unit, in particular via the second movement device.

As mentioned, the present invention further relates to a thawing device for thawing a substrate, in particular blood plasma, which is in a frozen aggregate state, the substrate being contained in a container, in particular a bag, the thawing device comprising a. a receiving unit for arranging the container containing the substrate, the receiving unit comprising heating means for providing thermal energy required for thawing the substrate;

b. a first movement device, which is set up to transmit a first movement to the receiving unit as well as the container received therein together with the substrate, wherein the first movement is a movement executed essentially in a plane, in particular a linear movement.

According to the invention, this thawing device is characterized by a further movement device which is set up to transmit a further movement to the receiving unit as well as to the container received therein together with the substrate, the further movement running in a different direction than the first movement and, in particular, running perpendicular to the plane in which the first movement is carried out.

The further movement device can be provided instead of the second movement device. In this way, a simplification of the thawing device can be achieved. The further movement device can be simpler than the second movement device.

The further movement can also be a linear movement.

By means of the further moving device, a faster distribution of the heated molecules of the substrate can be achieved. Responsible for this is the fast and intensive energy input which can be achieved by means of the further movement device. This faster molecule distribution can simultaneously cause a faster cooling of the molecule heating achieved by the heat input. This in turn can cause the thawing process to proceed very quickly, thus drastically shortening the thawing time.

The further movement transmitted by the further movement device to the receiving unit and the container received therein together with the substrate is preferably a further shaking movement in the sense of a back and forth movement executed in one plane. The first movement and/or the further movement can be executed with a frequency between 0.5 and 50 Hz. The first movement and/or the further movement may be executed with a frequency between 5 and 50 Hz and preferably comprise a movement of 1 to 20 mm or of 5 to 15 mm. The further shaking movement is preferably executed with a frequency of about 20 Hz and preferably comprises a movement of about 10 mm. The further movement can be a linear movement, but also a movement guided in a circle. More complex motion sequences (motion patterns) executed in a plane are also conceivable. The plane can be a vertical plane, but also a plane arranged elsewhere in space (e.g. inclined).

Preferably, the thawing device thus transmits two-preferably superimposed-shaking movements in different directions to the receiving unit as well as to the container and substrate received therein, preferably to the entire container and substrate. XY movements of the receiving unit and the container, preferably of the entire container, can be realized.

A tuning device can be provided which is set up to tune the frequency and/or phase position of the further movement to the frequency and/or phase position of the first movement. In this way, the superimposition of the first movement with the further movement can be optimized.

According to a further advantageous embodiment of the invention, it may be provided in a thawing device according to the invention that the further movement device comprises at least one movement unit. The further movement device may comprise a plurality of movement units. The further movement device may comprise exactly two movement units.

According to a further advantageous embodiment of the invention, it can be provided in a thawing device according to the invention that the at least one movement unit of the further movement device comprises a linear drive, which can be mechanically operatively connected to the receiving unit for transmitting the further movement. Preferably, the linear drive generates a translatory movement which can be transmitted to the receiving unit. In this case, the movement can be a linear movement or another movement with a predetermined course. The linear drive can be a threaded rod drive (ball screw drive), a roller screw drive, a hydraulic drive, a pneumatic drive or an electromechanical linear drive (e.g. a linear motor).

According to a further advantageous embodiment of the invention, it can be provided in a thawing device according to the invention that the linear drive of the further movement device is an electromechanical linear drive which has at least one stator arrangement and one rotor arrangement, it being possible for the rotor arrangement to be operatively connected to the receiving unit. The electromechanical linear drive is preferably a linear motor with which translatory feed movements can be generated. Preferably, the linear motor is based to a substantial extent on the Lorenz force. As already mentioned, a linear motor is a linear version of a rotating machine, which can be imagined as the unwinding of a rotary motor cut open to the center. It consists of a current-carrying primary part (comparable with the stator of a rotary motor, referred to here as the stator arrangement), and a reaction or secondary part (comparable with the rotor of a rotary motor, referred to here as the rotor arrangement). Linear motors can be synchronous linear motors, asynchronous linear motors, stepper linear motors or DC linear motors. While the stator arrangement in the asynchronous design is equipped with short-circuit bars, this consists of permanent magnets in the synchronous motor. Also, the linear drive of the further motion device can be a reluctance motor, which comprises a stator arrangement and a rotor arrangement. In this way, costs can be saved compared to a linear motor based substantially on the Lorenz force. However, a linear motor based substantially on Lorentz force can be controlled more precisely than a reluctance motor, which also allows higher peak values to be achieved. The motion of the rotor arrangement of the linear drive of the further motion device and the further motion are preferably not counter-rotating, but co-rotating.

According to a further advantageous embodiment of the invention, it can be provided in a thawing device according to the invention that a force transmission element is arranged between the receiving unit, in particular the lower half shell, and the at least one movement unit of the further movement device, which force transmission element can be connected both to the receiving unit, in particular the lower half shell, and to the at least one movement unit of the further movement device in order to transmit the further movement to the receiving unit, in particular the lower half shell. If a plurality of the movement units of the further movement device are provided, it is advantageous to provide a number of force transmission elements corresponding to the number of movement units, and to arrange these in each case between the receiving unit and the respective movement units and to connect them to both components. The force transmission element can be connected to a component belonging to the respective movement unit of the further movement device, for example a housing.

In addition to the further movement, the force transmission element can also be provided for transmitting the first movement.

According to a further advantageous embodiment of the invention, it can be provided in a thawing device according to the invention that the force transmission element has a flat force transmission area for transmitting force to the receiving unit. In this way, a deformation of the receiving unit, in particular of the lower half shell, can be avoided or reduced during the force transmission. Preferably, the linear drive of the further motion device is an electromechanical linear drive in the form of a linear motor based to a substantial extent on the Lorenz force and not, for example, a reluctance motor. Preferably, the linear actuator of the further motion device has a stator arrangement comprising stators and/or control windings and/or bases. Preferably, the stators are Fe stators. Preferably, the stators and/or the control windings are arranged spaced from the housing, for example housing base, by means of the bases.

Preferably, the stator assembly leaves a slot exposed, preferably between the control windings and the stators. Preferably, the slot is surrounded by the control windings and the stators. Preferably, the linear actuator of the further motion device comprises a rotor arrangement. Preferably, the rotor arrangement comprises at least one rotor. The rotor may comprise an Fe sheet or a permanent magnet. The permanent magnet may be a neodymium permanent magnet (NdFeB permanent magnet). Preferably, the rotor assembly comprises a force transmission element that further preferably transmits force between the rotor and the receiving unit. Preferably, the force transmission element has a planar force transmission area that can be connected to the pickup unit, for example in a force-locking and/or form-locking manner. The rotor can be connected to the force transmission element, for example in a force-locking and/or form-locking manner. The force transmission element may also be referred to as a fastening part. Preferably, the force transmission element comprises plastic, such as fiber-reinforced plastic and/or metal, such as aluminum. The force transmission element may be plate-shaped, preferably with a thickened end comprising the force transmission area. The force transmission element may be arranged in the slot of the stator arrangement, and it may be movable in the slot in the direction of the first movement and/or the further movement. Preferably, application of current to the control winding causes the rotor, and thus the force transmission element, to move back and forth in the direction of the further movement, and thus preferably causes the further movement to be transmitted to the receiving unit.

For the purpose of superimposing the first movement with the further movement, the linear drive of the first movement device can, for example, be connected to the pick-up unit by means of the force transmission element.

A guide arrangement can be provided for guiding the force transmission element in the slot, preferably in the direction of the first and/or the further movement. Preferably, the guide arrangement comprises a guide carriage which is movable-preferably in the direction of the first movement. Preferably, the guide carriage comprises guide wheels. Preferably, the guide wheels cooperate with a guide rail. The guide rail can be aligned in the direction of the first movement. The guide rail may be mounted to the housing, preferably the housing base, preferably by means of a base. Preferably, the guide arrangement comprises a connecting means between the guide carriage and the force transmission element. The connecting means may be connected to the force transmission element and the guide carriage. Preferably, the connecting means allows relative movement between the force transmission element and the guide carriage in the direction of the further movement and/or causes the force transmission element to be guided in the direction of the first movement and/or the further movement. The connecting means preferably comprises a steel spring blade. The steel spring leaf can be of planar design. The steel spring leaf may be at least substantially square in shape. The steel spring leaf may have a length of about 100 mm and a width of about 80 mm and a thickness of about 0.3 mm. The steel spring leaf may be attached to the force transmission element with one edge and to the guide carriage with an opposite edge. The guide arrangement for each force-transmitting element may comprise two connecting means attached to the force-transmitting element, preferably on both sides of the latter. In the case of two movement units of the further movement device arranged next to each other perpendicular to the first movement, the guide arrangement can also comprise exactly one connecting means for each force transmission element. The connecting means can be arranged on sides of the force transmission elements facing away from each other.

As mentioned, the above-mentioned task is also solved with a method for thawing a substrate in a frozen aggregate state, in particular blood plasma. In this case, the substrate is contained in a container, in particular a bag. The method is carried out with a thawing device according to the invention and comprises the following steps:

- a. Arrangement of the container containing the substrate in the receiving unit,
- b. Heating of the substrate contained in the container by means of the heating device, wherein during the heating process
  - i. a first movement is transmitted by the first movement device to the receiving unit and the container received therein together with the substrate, wherein the first movement is a movement executed substantially in one plane, in particular a linear movement, as well as
  - ii. a second movement is transmitted by the second movement device to the receiving unit and the container received therein together with the substrate, the second movement being a fulling movement.

The task is also solved by a method for thawing a substrate in a frozen aggregate state, in particular blood plasma, the substrate being contained in a container, in particular a bag, the method being carried out with a thawing device according to the invention, comprising the following steps:

- a. Arrangement of the container containing the substrate in the receiving unit,
- b. Heating of the substrate contained in the container by means of the heating device, wherein during the heating process
  - i. a first movement is transmitted by the first movement device to the receiving unit and the container received therein together with the substrate, wherein the first movement is a movement executed substantially in one plane, in particular a linear movement, as well as
  - ii. with the further movement device, a further movement is transmitted to the receiving unit and the container received therein together with the substrate, the further movement running in a different direction than the first movement and, in particular, running perpendicular to the plane in which the first movement is executed.

Figure 2:
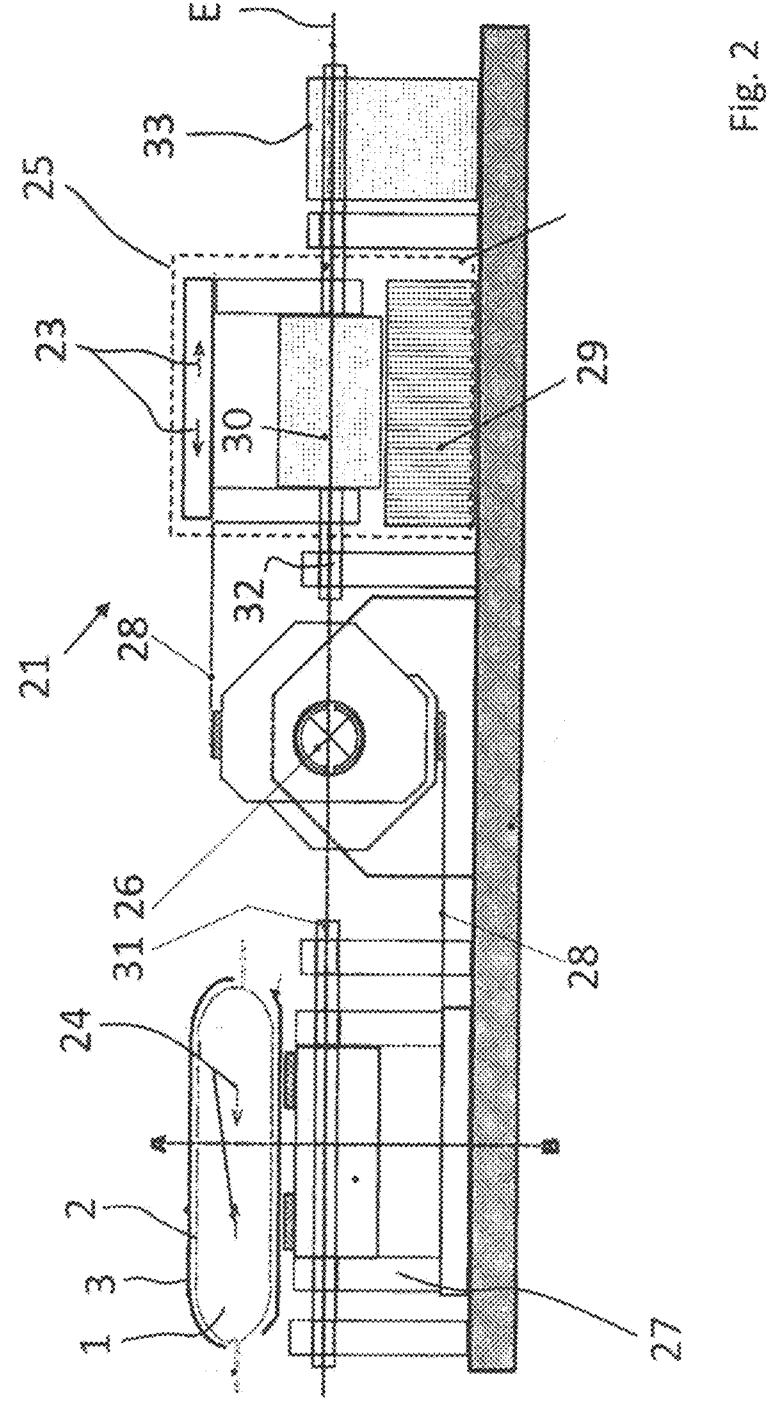
Figure 3:
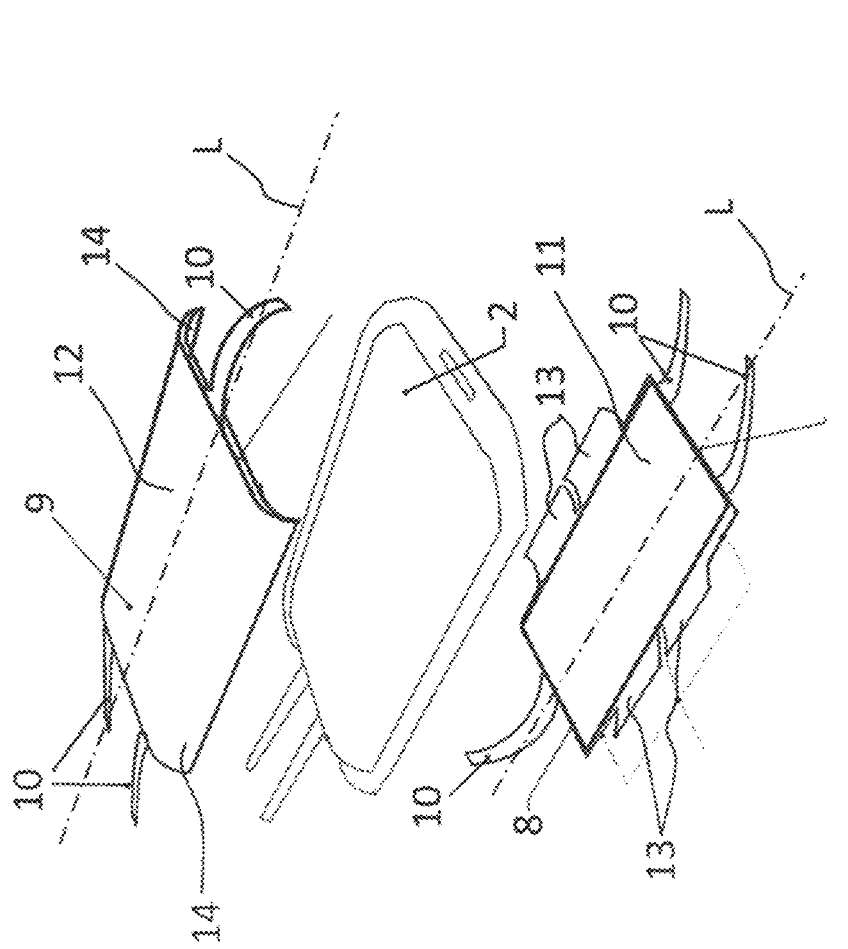
Figure 4:
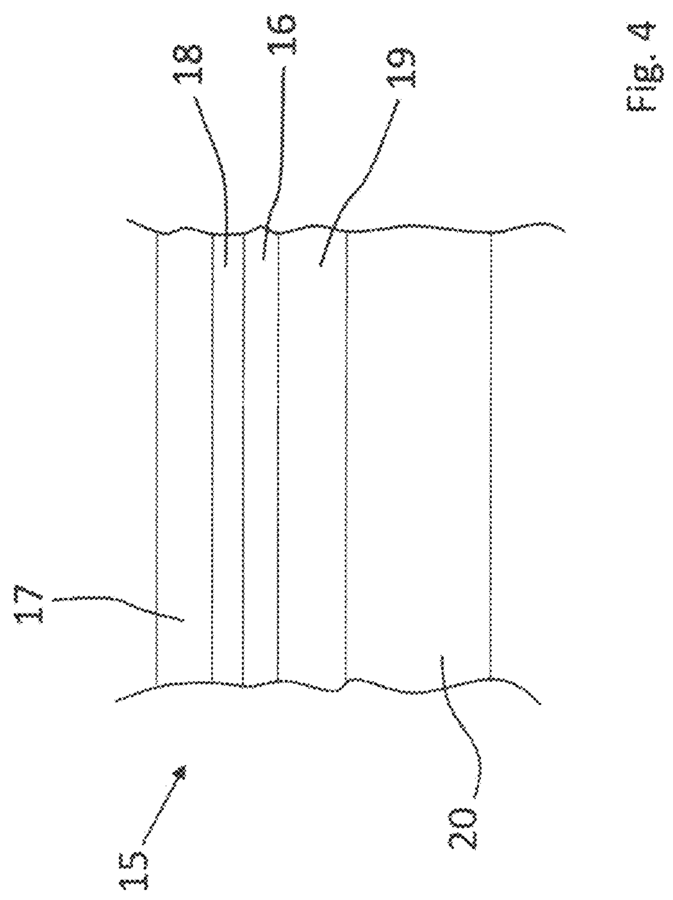
Figure 5:
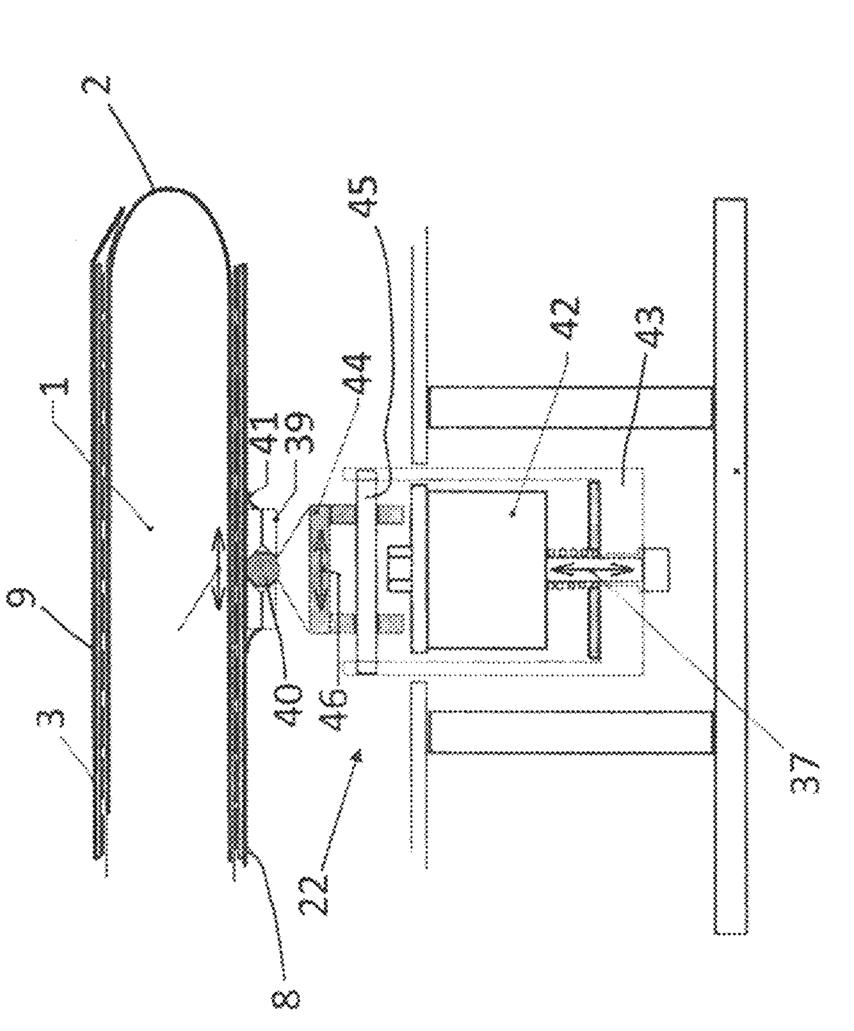
Figure 6:
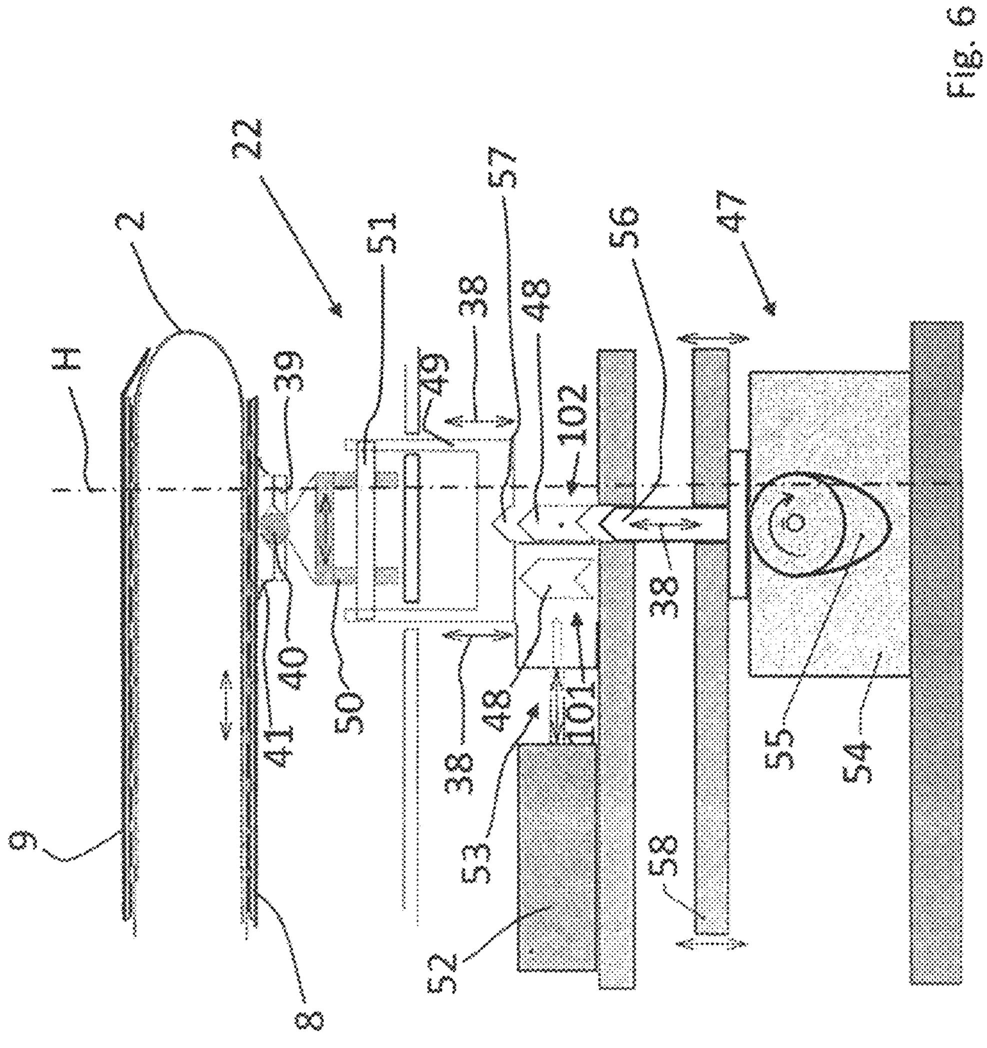
Figure 7:
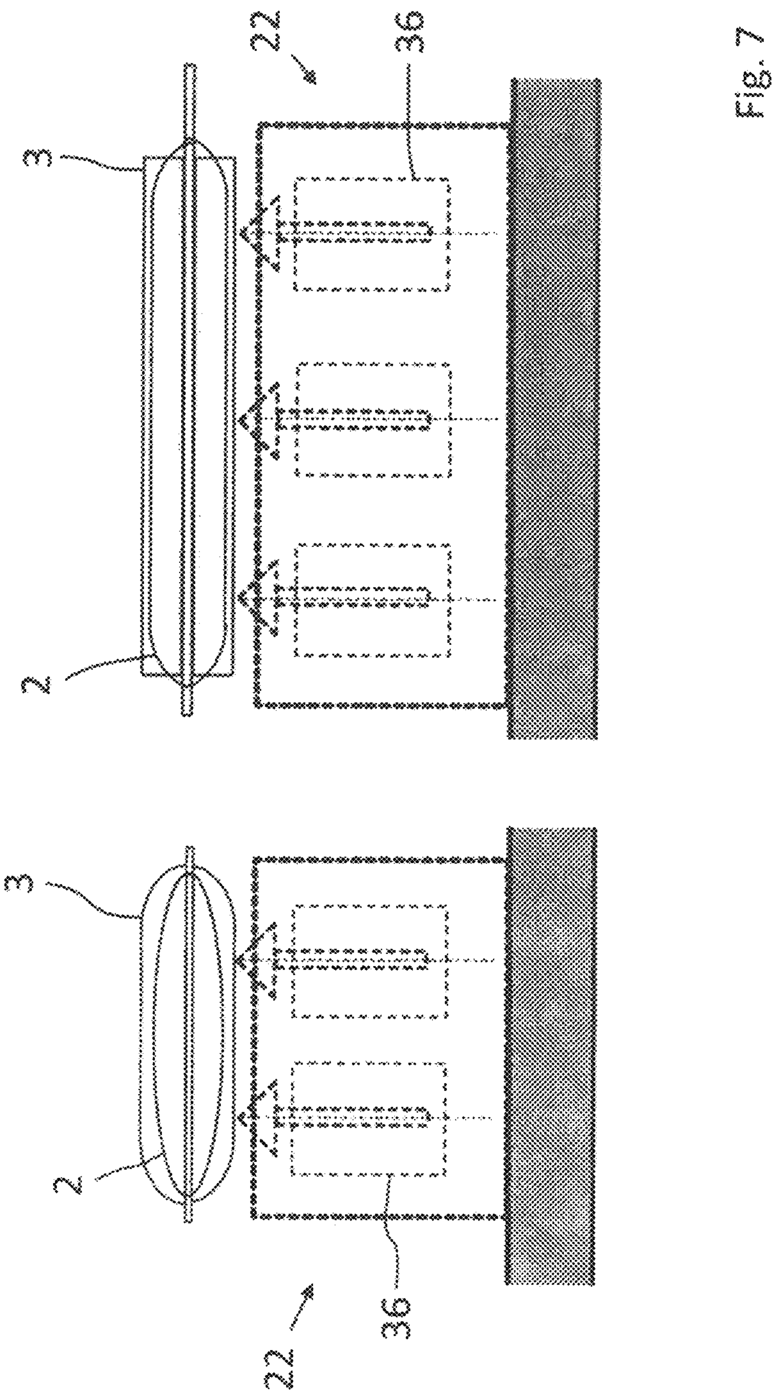
Figure 8:
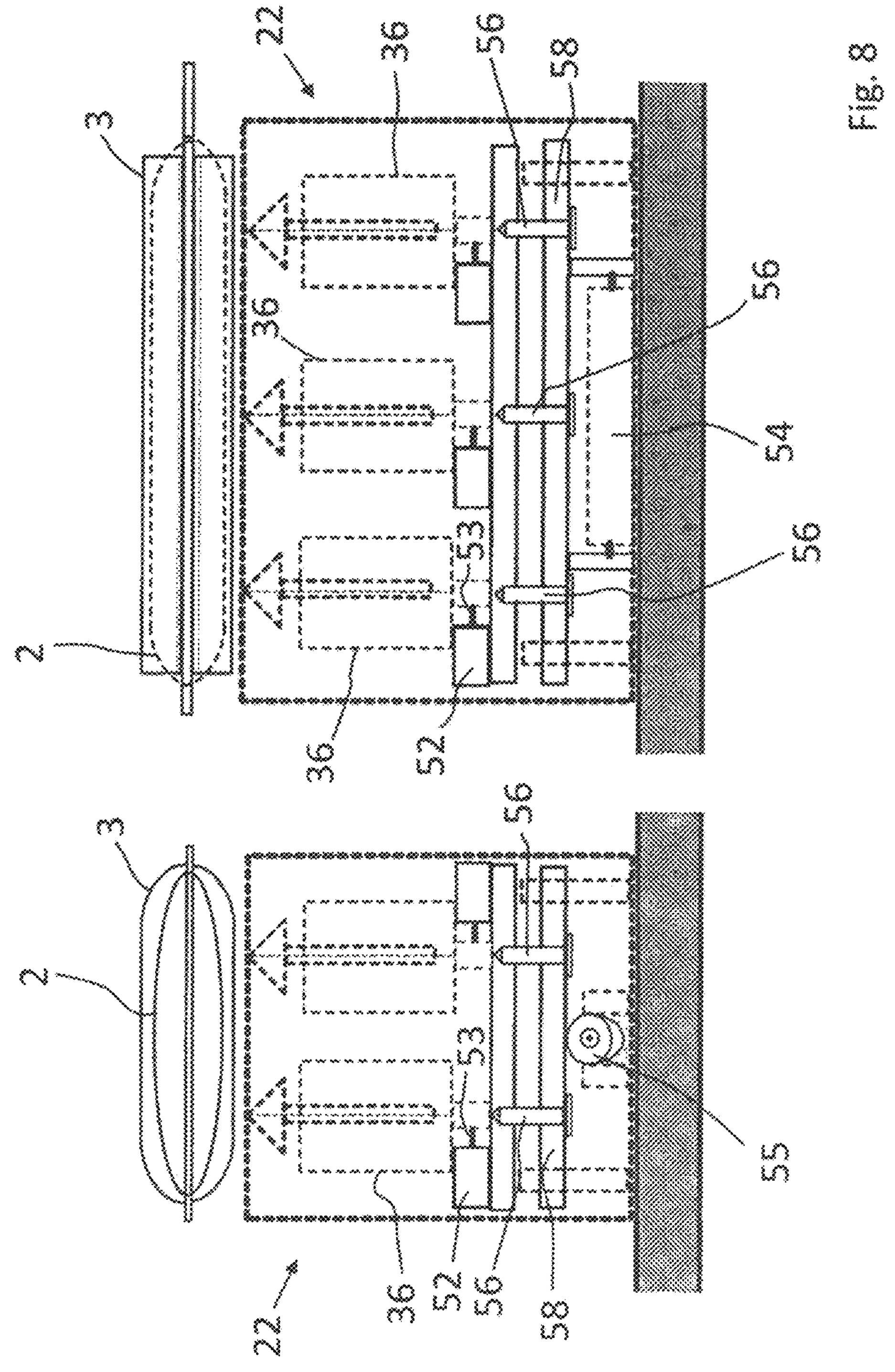
Figure 9:
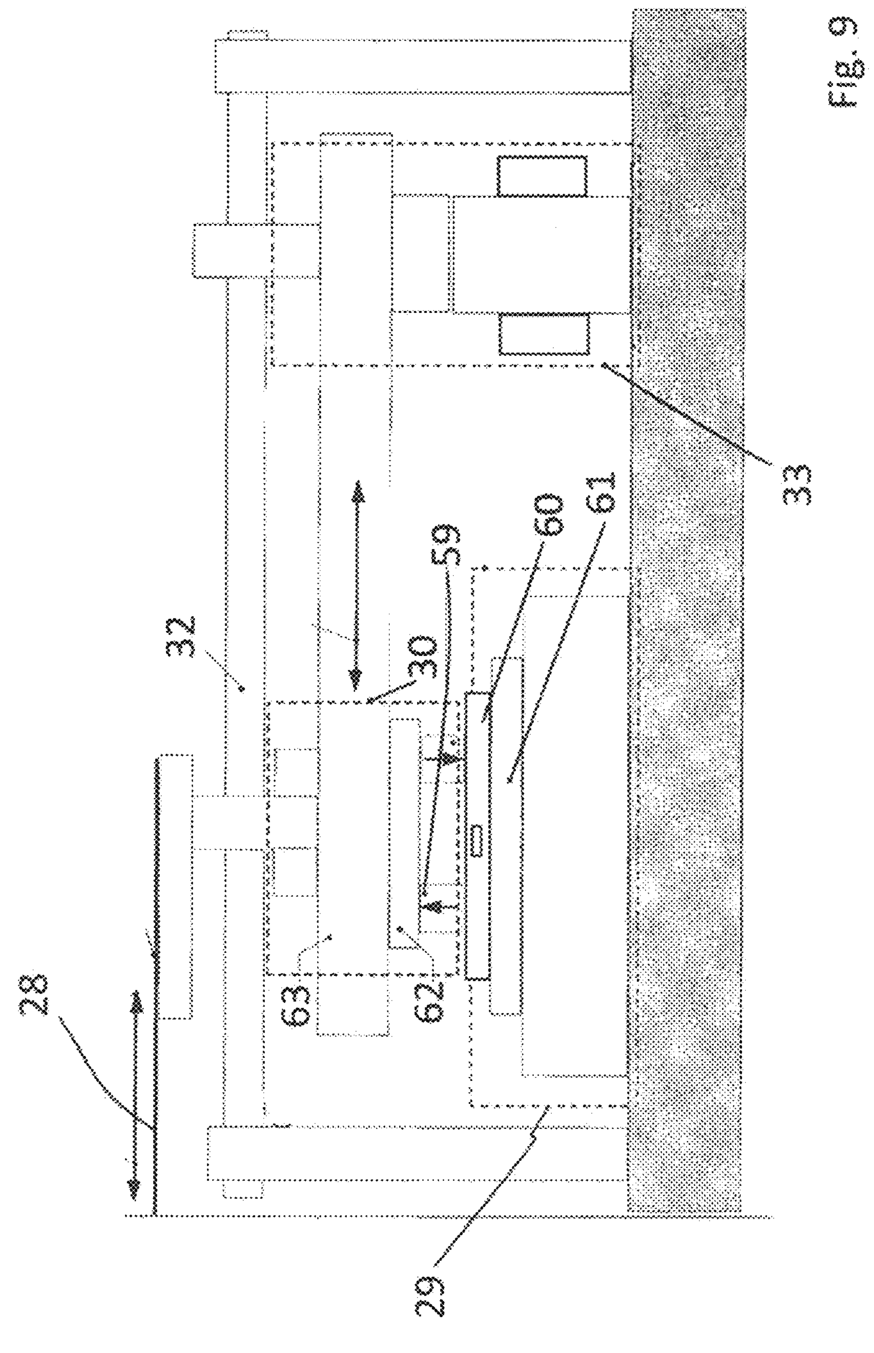
Figure 10:
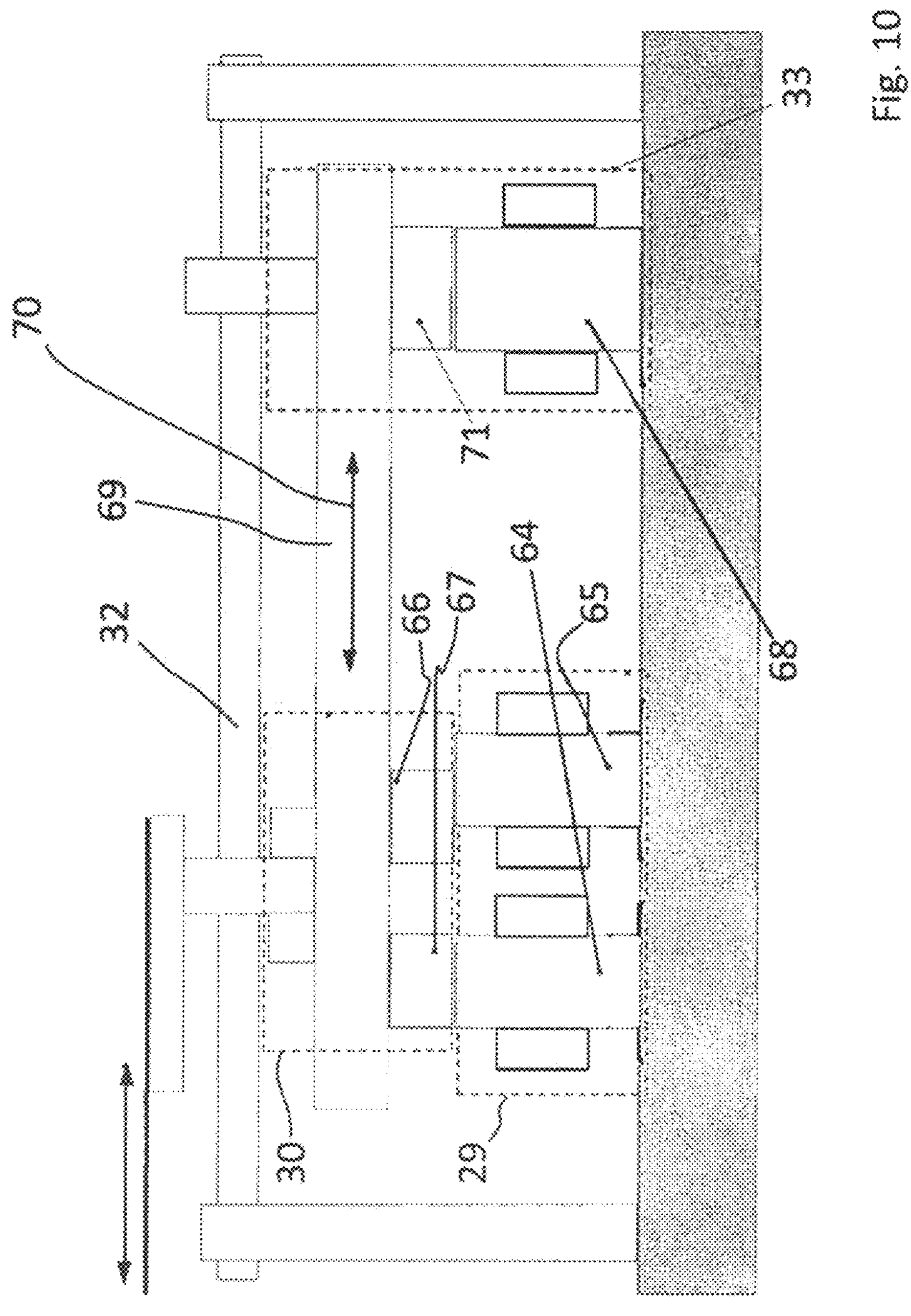
Figure 11:
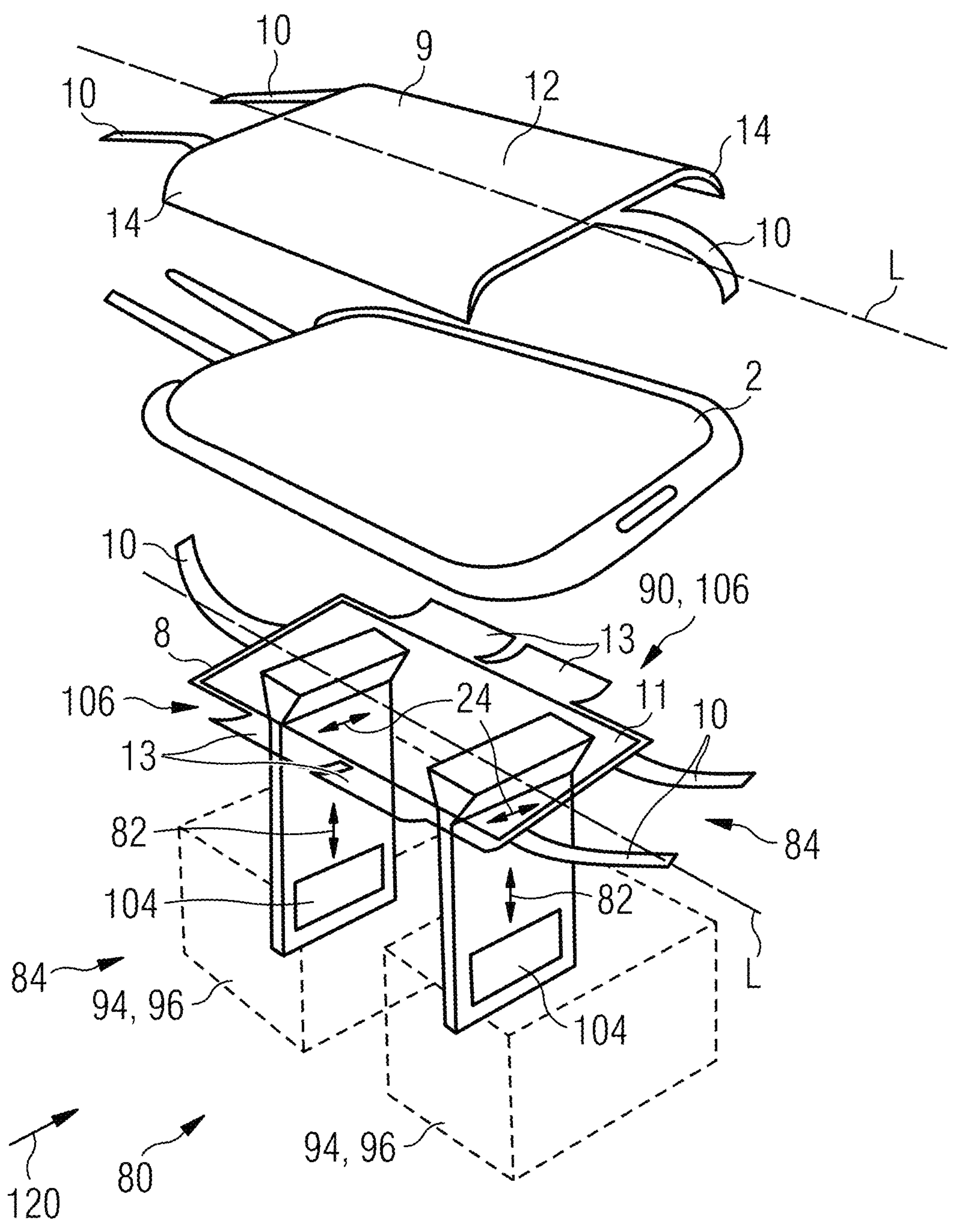
Figure 12:
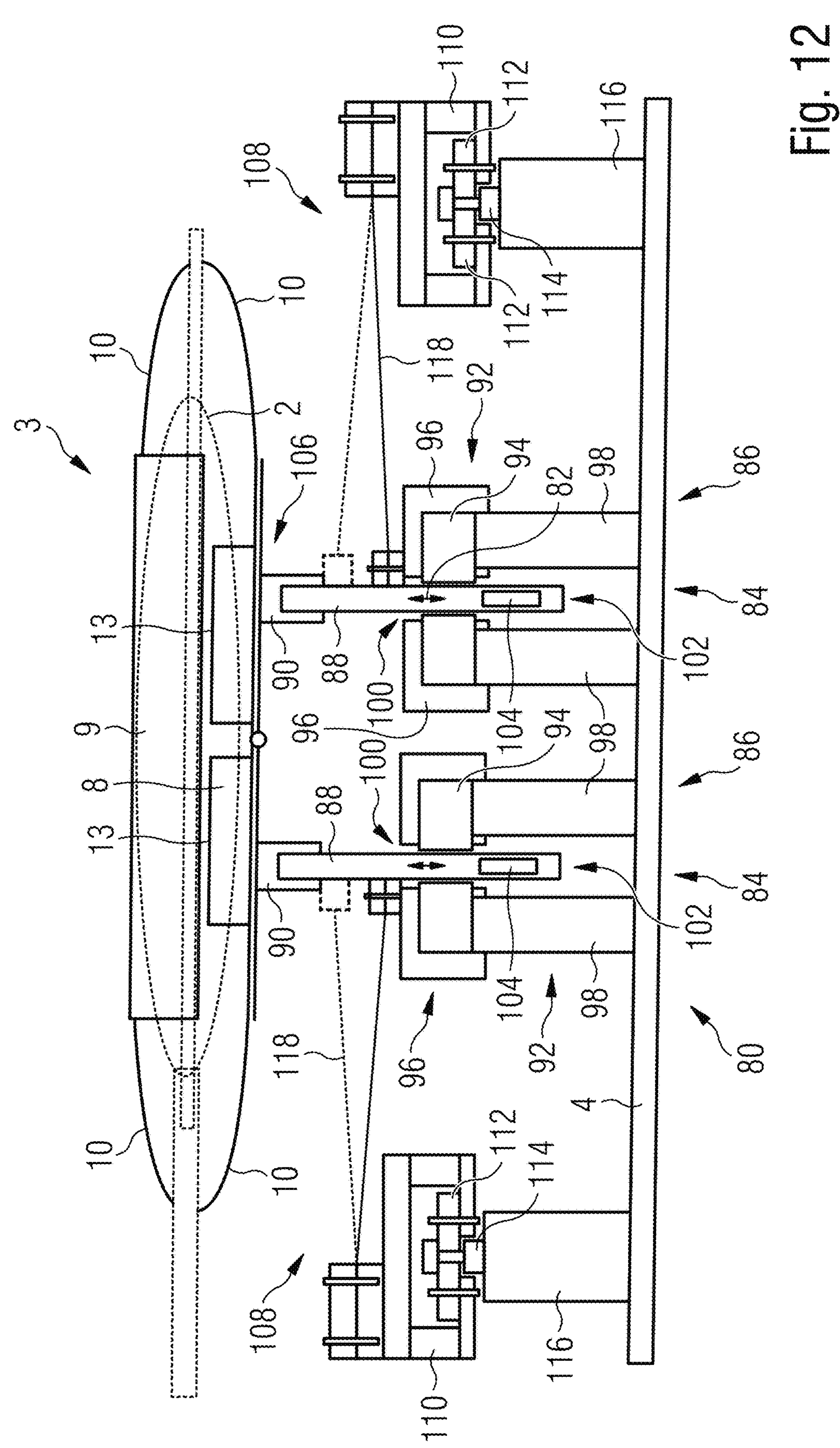

Further features and advantages of the invention will be apparent from the following description of non-limiting embodiments of the invention, which will be explained in more detail below with reference to the drawings. In these drawings show:

FIG. 1 a schematic representation of a thawing device according to the invention together with its essential components;

FIG. 2 a schematic representation of the thawing device according to the invention in longitudinal section, the representation showing in particular those components associated with the first movement device;

FIG. 3 a perspective view of a receptacle unit associated with the thawing device according to the invention, together with the receptacle;

FIG. 4 the layered structure of a half-shell associated with the receptacle unit according to FIG. 3;

FIG. 5 a schematic representation of a second motion unit associated with the second motion device in a first embodiment;

FIG. 6 a schematic representation of a second motion unit associated with the second motion device in a second embodiment;

FIG. 7 an illustration of a possible spatial arrangement of a plurality of second motion units according to FIG. 5;

FIG. 8 an illustration of a possible spatial arrangement of a plurality of second motion units according to FIG. 6;

FIG. 9 a schematic representation of the structure of an electromechanical linear actuator together with an electric spring system;

FIG. 10 a schematic diagram of the design of a reluctance motor as a linear drive including an electric spring system;

FIG. 11 an exploded perspective view of a portion of a further embodiment;

FIG. 12 a side view looking in the direction of arrow 120 of the embodiment shown in FIG. 11.

FIG. 1 shows a schematic representation of the structure of a thawing device according to the invention for thawing a substrate 1 in a frozen aggregate state. The substrate 1 may in particular be blood plasma. The frozen substrate 1 is contained in a container 2, in particular a bag.

The thawing device has a housing 4 which can be opened via an opening flap 5. The opening flap 5 is hinged or pivotably mounted on the housing 4 via a hinge 6. Inside the housing 5 a receiving unit 3 is arranged, in which the container 2 (together with substrate 1) can be arranged or inserted. For the following explanations it is assumed that the container 2 is a form-flexible blood plasma bag. The receiving unit 3 comprises a heating device (not shown in FIG. 1) for providing thermal energy required for thawing the substrate. The receiving unit 3 is in the form of a tray, the tray comprising a first half-shell 8 and a second half-shell 9. The first half-shell 8 provides a lower half-shell and the second half-shell 9 provides an upper half-shell. The half shells 8, 9 can be detachably connected to each other. The first half-shell 8 and second half-shell 9 are adapted to the shape of the container 2, wherein the first and second half-shells 8, 9 at least partially surround the container 2 when it is arranged in the shell (cf. FIG. 1).

As shown in detail in FIG. 3, fixing means 10 in the form of retaining clips are arranged on the first and second half shells 8, 9, with which the container 2 can be fixed in the shell formed by the half shells 8, 9. Furthermore, the half shells 8, 9 can be connected to each other by means of the fixing means 10. The half-shells 8, 9 have a rectangular half-shell base 11, 12, the shell shape being provided by side wall portions 13, 14 adjacent to side regions of the half-shell base 11, 12 and extending along a half-shell longitudinal axis L. Preferably, those side wall sections 13 of the lower half-shell 8 are designed to be flexible, while the side wall sections 14 of the upper half-shell 9 are designed to be dimensionally stable, i.e. rigid. The fixing means 10, which are in the form of retaining clips, can be fastened to the opposing half shells 8, 9 by suitable fastening devices.

The first and second half-shells 8, 9 each have a multi-layer layer structure 15 (FIG. 4), with a heating element 16 being provided in one layer of the layer structure 15 of a respective half-shell 8, 9. The heating elements 16 of the respective half shells 8, 9 provide the heating device. The heating elements 16 may extend along the half-shell 8, 9 (in particular over the surface of the half-shell base 11, 12) in a meandering or spiral manner, wherein the heating elements 16 are formed of stainless steel. Preferably, the heating elements 16 have a thickness of 50 μm. The respective heating element 16 can also be in the form of a heating foil.

The multilayer structure 15 of the half-shells 8, 9 is composed as follows (see FIG. 4). Facing the container 2 arranged in the receiving unit 3, the half-shells 8, 9 have an outer skin 17 or a support layer for supporting the container 2. This is preferably made of stainless steel and has a layer thickness of 100 μm to 150 μm. This is followed by an electrical insulation layer 18, preferably 50 μm thick, which can be made of a polyimide film, for example. The layer comprising the heating element 16 adjoins the insulation layer 18, and this layer can have a thickness of 50 μm. The layer comprising the heating element 16 can also be in the form of a stainless steel foil, but can also be made of an electrically insulating material in which one or more heating elements 16 made of stainless steel are integrated. This is followed by a support or insulation layer 19, which is preferably formed from a glass-fiber-reinforced plastic and has a thickness of 0.3 mm. This is followed by a mounting support 20 for the respective half shell 8, 9, which is made of aluminum and has a thickness of 0.5 to 1.0 mm.

As shown in FIG. 1, a further component of the thawing device is the collecting tray 7 arranged in the housing 4 below the receiving unit 3, which prevents moisture or other impurities arising during the thawing process (for example substrate 1 escaping through a leak in the container 2) from reaching places in the thawing device where, for example, electrical components could be damaged. The collection tray 7 is preferably designed and arranged in such a way that it can be removed from the housing 4 for emptying.

A first movement device 21 is arranged in the housing 4, which is set up to transmit a first movement (characterized by the movement arrows 24) to the receiving unit 3 as well as the container 2 received therein together with the substrate 1. The first movement is a movement executed essentially in a plane, in particular a linear movement. The first movement device 21 comprises a linear drive 25, which is mechanically operatively connected via a mechanical coupling device 26 to at least one movably mounted guide unit 27 (FIG. 2), the at least one guide unit 27 being mechanically operatively connected to the receiving unit 3 for transmitting the first movement.

The mechanical coupling device 26 is a universal joint which is arranged between the linear drive 25 and the at least one guide unit 27 and is connected both to the linear drive 25 and to the at least one guide unit 27 or to a component operatively connected thereto via a connecting means 28, for example a stainless steel strip. The linear drive 25 is an electromechanical linear drive which has at least one stator arrangement 29 and a rotor arrangement 30, the rotor arrangement 30 being connected to the mechanical coupling device 26 via the connecting means 28, in particular the stainless steel strip. The at least one guide unit 27 and the rotor arrangement 30 are each movably mounted on guide rods 31, 32, the guide rods 31, 32 being arranged in a common plane E. If the rotor arrangement 30 is set in motion (cf. the motion arrows 23), this motion is transmitted to the guide unit 27 by the mechanical coupling device 26. The guide unit 27 also undergoes a movement (cf. the movement arrows 24), but this movement is in the opposite direction to that of the slider arrangement 30.

Furthermore, the thawing device has a second movement device 22, which is set up to transmit a second movement to the receiving unit 3 and the container 2 received therein together with the substrate 1, the second movement being a fulling movement. In FIG. 1, it is schematically shown that the second movement device 22 has a plurality of second movement units 36 which transmit a movement to the receiving unit 3 at a plurality of positions. The same is reproduced in FIGS. 7 and 8.

The second movement device 22 thus comprises at least one, preferably several, second movement unit(s) 36, wherein the at least one second movement unit 36 is set up to exert a lifting movement (cf. e.g. the movement arrow 37 in FIG. 5 and the movement arrows 38 in FIG. 6, all characterizing vertical lifting movements) on the receiving unit 3, in particular the lower half-shell 8, wherein a partial deformation of the receiving unit 3, in particular of the lower half-shell 8, is effected to an extent corresponding to a thawed portion of the substrate 1 when the lifting movement is exerted.

The second movement units 36 are arranged at different spatial positions in order to exert a lifting movement on the receiving unit 3, in particular the lower half shell 8, so that a fulling movement is generated by the plurality of lifting movements.

FIGS. 5 and 6 show different designs of second movement units 36. However, both variants have in common that a force transmission element 39 is arranged between the receiving unit 3, namely the lower half shell 8, and the at least one second movement unit 36, which force transmission element 39 is connected both to the receiving unit 3 (the lower half shell 8) and to the at least one second movement unit 36 in order to transmit the lifting movement to the receiving unit 3, namely the lower half shell 8. The force transmission element 39 has a ball bearing 40 and is attached to the lower half shell 8 via a welded connection 41.

According to the embodiment example shown in FIG. 5, the at least one second movement unit 36 comprises at least one lifting magnet 42, which is set up to transmit a stroke, in particular a lifting and lowering stroke, to the force transmission element 39, the receiving unit 3 connected to the force transmission element 39, and the container 2 arranged in the receiving unit 3, together with the substrate 1 contained therein, by carrying out lifting movements (cf. the movement arrow 37). If the second movement device 22 comprises a plurality of second movement units 36, each of the second movement units 36 may comprise a lifting magnet.

When the lifting movement (FIG. 5) is executed, the stroke is first transmitted from the lifting magnet 42 to a linkage 43 (or a housing part) associated with the second movement unit 36. The linkage 43 (or housing part) is connected to a movably mounted carriage 44, the carriage 44 in turn being connected to the force transmission element 39. The carriage 44 is movably mounted on a guide rod 45 in such a way that it tracks the first movement (shaking movement) triggered by the linear actuator 25 (see the movement arrow 46). The movable mounting of the carriage 44 has the effect that the second movement units 36 (for generating the fulling movement) are decoupled from the first movement or the associated oscillations. Thus, the second movement units 36 do not follow the first movement.

According to the embodiment example shown in FIG. 6, the at least one second movement unit 36 comprises at least one mechanical lifting device 47, which is set up to transmit a stroke, in particular a lifting and lowering stroke, to a force transmission pin 48 arranged so as to be movable transversely, in particular perpendicularly, to the stroke axis H by carrying out lifting movements.

In this case, the force transmission pin 48 can be moved transversely, in particular perpendicularly, to the stroke axis H between a first position 101 and a second position 102. In its second position 102, the force transmission pin 48 transmits a lifting movement generated by the mechanical lifting device 47 to the force transmission element 39, the receiving unit 3 connected to the force transmission element 39, and the container 2 arranged in the receiving unit 3 together with the substrate 1 contained therein. In particular, the force transmission pin 48 is set up to transmit, in its second position 102, a lifting movement generated by the mechanical lifting device 47 to a housing part 49 in which a carriage 50 connected to the force transmission element 39 is movably mounted. The carriage 50 is movably mounted on a guide rod 51 arranged in the housing part 49. The movable mounting of the carriage 50 has the effect that the second movement unit 36 is decoupled from the first movement device 21 and the first movements generated thereby.

In the first position 101 of the force transmission pin 48, no transmission of the stroke movement takes place in the direction of the force transmission element 39. The force transmission pin 48 is controlled by a control unit 52 and moved back and forth transversely, in particular perpendicularly, to the stroke axis via a movement mechanism 53. In this embodiment, the stroke movement is generated by a geared motor 54, which drives a camshaft 55 at approximately 60 rpm. The motion is first transmitted to a plunger 56 connected to the camshaft 55 and arranged for linear movement along the stroke axis H, the plunger 56 engaging a (lower) end of the power transmission pin 48 in the second position 102 of the power transmission pin 48 and transmitting the stroke motion thereto. Meanwhile, a recess 57 is formed at the lower end of the housing portion 49 to correspond to an upper end of the force transmission pin 48 and to provide a positive fit. A plunger plate 58 may be provided to arrange a plurality of plungers 56.

FIG. 7 illustrates how the second movement units 36 (according to the design variant shown in FIG. 5 including lifting magnets 42) can be distributed or arranged over the width of the pick-up unit 3 (shown on the left) and over the length of the pick-up unit 3. In this variant, a total of six second movement units 36 with a total of six lifting magnets 42 are provided.

In analogy to FIG. 7, FIG. 8 also illustrates a distribution of the second movement units 36, but in an embodiment according to FIG. 6 (mechanical lifting device 47). In the left-hand illustration, the distribution of the second movement units 36 over the width of the receiving unit 3 is reproduced, while in the right-hand illustration, the distribution of the second movement units 36 over the length of the receiving unit 3 is shown. As shown, six plungers 56 are arranged on a common plunger plate 58. The plunger plate 58, and thus the plungers 56, are set in a reciprocating motion by use of a geared motor 54 and a camshaft 55. As described in the embodiment example of FIG. 6, each plunger 56 is associated with a force transmission pin 48, each of which can assume a first position 101 and a second position 102. Accordingly, each of the six force transmission pins 48 is assigned a control unit 52 and a movement mechanism 53.

The linear actuator 25 is connected to a mechanical or electrical spring system 33, which is arranged to adjust running characteristics and efficiency of the linear actuator 25. In particular, the spring system 33 is designed to improve the vibration circuit of the shaker drive (first motion device) while providing smoother running.

FIG. 9 shows an electric spring system in combination with an electromechanical linear actuator 25, in particular a permanent magnet linear motor as linear actuator 25. Such a linear actuator 25 comprises the following components: Neodymium permanent magnets 59, a Cu flat coil 60, a laminated Fe stator return 61, a laminated Fe rotor return 62, and a rotor bearing 63 with sliding bearings. The electric spring system 33 is connected to or operatively coupled with the permanent magnet linear motor via the rotor bearing 63.

In FIG. 10, the electric spring system 33 is shown in conjunction with a reluctance motor which replaces the permanent magnet linear motor shown in FIG. 9. Reluctance motors are generally known from the prior art and concern a special design of an electric motor in which a force torque is generated solely by reluctance force and not to a substantial extent by Lorentz force, as is the case with magnetically excited machines.

In combination with the electric spring system 33 acts like the reluctance motor. The transformer 64 shown on the left in FIG. 10 behaves magnetically neutral and remains without current. A leaded yoke 67 is associated with the left transformer 64. The right transformer 65 is supplied with current at a certain point in time, so that a force proportional to the amount of applied current is generated to the right and the left transformer 64 remains without current supply at the same time. When the yoke 66 of the right transformer 65 has now reached a neutral position, the 35 procedure described above is repeated, but in the opposite direction. The electrical spring system 33 (transformer 68) has somewhat larger dimensions than the reluctance transformers 64, 65. The transformer 68 of the spring system 33 is continuously energized, with the result that it remains in neutral position (despite current flow) and does not exert any forces (cf. the yoke position of the leaded yoke 71). If the reluctance motor now moves the slide 69 (cf. the movement arrow 70), the spring system 33 generates a force which counteracts the force of the reluctance motor. The decisive factor here is that the current of the spring system is set so that the entire drive system is supported by the spring force and the maximum mechanical deflection is achieved with the lowest current flow of the reluctance motor.

Further components of the thawing device are—as shown in FIG. 1—devices of the power electronics 34 and electronics 35.

FIGS. 11 and 12 show a further embodiment in which a further movement device 80 is provided instead of the second movement device. The further movement device is set up to transmit a further movement (characterized by the movement arrows 82) to the receiving unit 3 and the container 2 received therein together with the substrate. The further movement is a vertical linear movement and runs perpendicular to the linear movement of the first movement. In the embodiment example shown in FIGS. 11 and 12, the further movement is not a fulling movement.

The receptacle unit 3 is flexible or deformable. Alternatively, the holder unit 3 or one or both of the half shells 8, 9 could be dimensionally stable, i.e. rigid.

The further movement is another shaking movement. The thawing device thus transmits two superimposed shaking movements in different directions to the receiving unit 3 and the entire container 2 received therein, including the entire substrate. An XY movement of the receiving unit 3 and of the entire container 2 can be realized.

The further motion device 80 includes two motion units 84 of the further motion device 80. These motion units 84 each include a linear actuator 86.

The linear drive 86 is mechanically operatively connected to the pick-up unit 3 in each case to transmit the further movement.

A force transmission element 88 is arranged between the lower half shell 8 and each of the two movement units 84, and is connected both to the lower half shell 8 and to one of the two further movement units 84 in order to transmit the further movement to the lower half shell 8.

The force transmission element 88 has a flat force transmission area 90 for transmitting force to the pick-up unit 3. This prevents deformation of the pick-up unit 3, at least to a large extent.

The linear actuator 86 of the further motion unit 84 is an electromechanical linear actuator based in substantial part on the Lorenz force in the form of a linear motor and not, for example, a reluctance motor.

The linear actuator 86 has a stator assembly 92 that includes stators 94, control windings 96, and bases 98. The stators 94 are Fe stators and together with the control windings 96 are spaced from the housing 4, namely the housing base, by means of the bases 98.

The stator assembly 92 leaves a slot 100 exposed, surrounded by the control windings 96 and stators 94.

The movement of the rotor arrangement 102 of the linear drive 86 of the movement unit 84 and the further movement are in the same direction.

The rotor assembly 102 includes one rotor 104 at a time. The rotor is an Fe sheet or a permanent magnet.

The slider assembly 102 includes force transfer member 88, which transfers force between the slider 104 and the receiving unit 3.

The force transmission area 90 of the force transmission element 88 is positively and non-positively connected to the receiving unit 3. And the slider 104 is connected to the force transmission element 88. The force transmission element 88 is plate-shaped, with a thickened end comprising the force transmission region 90 106. The force transmission element 88 is arranged in the slot 100 of the stator arrangement 92 and is movable therein in the direction of the first movement and the further movement. An application of current to the control winding 96 causes the rotor 104, and thus the force transmission element 88, to move back and forth in the direction of the further movement and thus transmit the further movement to the receiving unit 3.

For the purpose of superimposing the first movement on the further movement, the linear drive 25 of the first movement device 21 can, for example, be connected to the receiving unit 3 by means of the force transmission element 88 (not shown in FIGS. 11, 12).

There are two guide arrangements 108 for guiding the two force transmission elements 88 in the slot 100 in the direction of the first movement and the further movement. The guide arrangements 108 each comprise a guide carriage 110 movable in the direction of the first movement and having guide wheels 112. The guide wheels 112 cooperate with a guide rail 114 oriented in the direction of the first movement. The guide rail 114 is mounted to the housing 4, namely the housing base, by means of a base 116. The guide arrangements 108 each comprise a connecting means 118 between the guide carriage 110 and the force transmission element 88, which allows a relative movement between the force transmission element 88 and the guide carriage 110 in the direction of the further movement or causes a guidance of the force transmission element 88 in the direction of the first movement and the further movement. The connecting means 118 is configured as a planar steel spring blade. The steel spring blade is attached to the force transmission element 88 with one edge and to the guide carriage 110 with the opposite edge.

The two motion units 84 are arranged side by side perpendicular to the first motion. The guide arrangements 108 comprise exactly one connecting means 118 for each force transmission element 88. The connecting means 118 are arranged on sides of the force transmission elements 88 facing away from each other.

LIST OF REFERENCE SIGNS

1 Substrate
2 Container
3 Acquisition unit
4 Housing
5 Opening flap
6 Hinge
7 Collecting tray
8 first half shell
9 second half shell
10 Fixer 11 Half-shell base
12 Half-shell base
13 Side wall section
14 Side wall section
15 Layer structure
16 Heating element
17 Outer skin
18 electrical insulation layer
19 Carrier or insulation layer
20 Mounting bracket
21 first movement device
22 second movement device
23 Motion arrow
24 Motion arrow
25 Linear actuator
26 mechanical coupling device
27 Guide unit
28 Lanyards
29 Stator arrangement
30 Rotor arrangement
31 Guide rod
32 Guide rod
33 Spring system
34 Power Electronics
35 Electronics
36 second movement unit
37 Motion arrow
38 Motion arrow
39 Force transmission element
40 Ball bearing
41 Welded joint
42 Solenoid
43 Linkage
44 Sledge
45 Guide rod
46 Motion arrow
47 mechanical lifting device
48 Force transmission pin
49 Housing part
50 Sledge
51 Guide rod
52 Control unit
53 Movement mechanics
54 Gear motor
55 Camshaft
56 Plunger
57 Recess
58 Plunger plate
59 Neodymium permanent magnets
60 Cu flat coil
61 Sheet Fe Stator Reverse
62 Leaded Fe-Runner Reverse
63 Runner camp
64 Transformer
65 Transformer
66 Yoke
67 Yoke
68 Transformer
69 Sledge
70 Motion arrow
80 further movement device
82 Motion arrow
84 further movement unit
86 Linear drive
88 Force transmission element
90 Force transmission range
92 Stator arrangement
94 Stator
96 Control winding
98 Socket
100 Slot
102 Rotor arrangement
104 Runners
106 thickened end
108 Guide arrangement
110 Guide carriage
112 Guide wheels
114 Guide rail
116 Socket
118 Fasteners
120 Arrow
E Ebene
H Lifting axis
L Half shell longitudinal axis

The invention claimed is:

1. A thawing device for thawing a substrate in a frozen aggregate state, the substrate being contained in a container, the thawing device comprising:
- a receiving unit for arranging the container containing the substrate, the receiving unit having a heating device for providing thermal energy required for thawing the substrate;
- a first movement device configured to transmit a first movement to the receiving unit and the container received therein together with the substrate, wherein the first movement is a movement executed essentially in a horizontal plane; and
- a second movement device configured to transmit a second movement to the receiving unit and the container received therein together with the substrate, wherein the second movement is a fulling movement,
- wherein the second movement device comprises at least one second movement unit configured to exert a vertical lifting movement on the receiving unit, wherein, when the vertical lifting movement is exerted, a partial deformation of the receiving unit is produced, the partial deformation having an extent corresponding to a thawed portion of the substrate.

2. The thawing device of claim 1, wherein the receiving unit is formed in the shape of a shell, wherein the shell comprises a first half shell and a second half shell, wherein the first half shell is a lower half shell and the second half shell is an upper half shell, and wherein the first and second half shells are detachably connectable to each other.

3. The thawing device of claim 2, wherein the first and second half-shells are adapted to the shape of the container, the first and second half-shells at least partially surrounding the container when the container is placed in the shell.

4. The thawing device of claim 2, wherein fixing means are provided on the first and second half-shells, with which the container can be fixed.

5. The thawing device of claim 2, wherein the first and second half shells each have a multilayer structure having a heating element provided in one layer of the multilayer structure of a respective half shell.

6. The thawing device of claim 1, wherein the first movement device comprises a linear drive in mechanical operative connection with at least one movably mounted guide unit via a mechanical coupling device, the at least one guide unit being mechanically operatively connected to the receiving unit for transmitting the first movement.

7. The thawing device of claim 6, wherein the mechanical coupling device is a universal spring joint arranged between the linear drive and the at least one guide unit and is connected both to the linear drive and to the at least one guide unit or to a component operatively connected thereto via a connecting means.

8. The thawing device of claim 6, wherein the linear drive is connected to a mechanical or electrical spring system, which is adapted to adjust running characteristics and efficiency of the linear drive.

9. The thawing device of claim 6, wherein the linear drive is an electromechanical linear drive, which has at least one stator and one rotor arrangement, the rotor arrangement being connected to the mechanical coupling device via a connecting means.

10. The thawing device of claim 9, wherein the at least one guide unit and the rotor arrangement are each movably mounted on guide rods, the guide rods being arranged in a common plane.

11. The thawing device of claim 1, wherein a force transmission element is arranged between the receiving unit and the at least one second movement unit, which force transmission element is connected both to the receiving unit and to the at least one second movement unit in order to transmit the lifting movement to the receiving unit.

12. The thawing device of claim 11, wherein the force transmission element comprises a ball bearing, and the force transmission element is fastened to the receiving unit, via a welded joint.

13. The thawing device of claim 1, wherein the at least one second movement unit comprises at least one lifting magnet, which is set up to transmit a stroke to the force transmission element, the receiving unit connected to the force transmission element and the container arranged in the receiving unit together with the substrate contained therein, by carrying out lifting movements.

14. The thawing device of claim 1, wherein the at least one second movement unit comprises at least one mechanical lifting device, which is set up to transmit a stroke to a force transmission pin arranged movably transversely to the stroke axis by carrying out lifting movements.

15. The thawing device of claim 14, wherein the force transmission pin can be moved transversely to the stroke axis between a first and a second position, the force transmission pin being arranged to, in its second position, transmit a lifting movement executed by the at least one mechanical lifting device to the force-transmitting element, the receiving unit connected to the force-transmitting element and the container arranged in the receiving unit, together with the substrate contained therein.

16. The thawing device of claim 1, wherein a further movement device is provided, which is set up to transmit a further movement to the receiving unit and the container received therein together with the substrate, the further movement running perpendicular to the plane in which the first movement is executed.

17. A method for thawing a substrate with the thawing device according to claim 1, wherein the substrate is in a frozen aggregate state, and wherein the substrate is contained in a container, the method comprising:

arranging the container containing the substrate in the receiving unit, heating the substrate contained in the container with the heating device, wherein during the heating process:

a first movement is transmitted by the first movement device to the receiving unit and the container received therein together with the substrate, the first movement being a movement executed substantially in a horizontal plane, and a second movement is transmitted by the second movement device to the receiving unit and the container received therein together with the substrate, the second movement being a fulling movement.

18. The thawing device of claim 1, wherein the second movement device comprises two or more of the second movement units arranged at different spatial positions, each of the two or more second movement units being configured to exert the vertical lifting movement on the receiving unit, wherein, when the vertical lifting movement is exerted by each of the two or more second movement units, a respective partial deformation of the receiving unit is produced at a corresponding spatial position.

* * * * *